United States Patent
Gopinath et al.

(10) Patent No.: US 11,461,902 B2
(45) Date of Patent: *Oct. 4, 2022

(54) SYSTEMS AND METHODS TO DETECT AND DISPLAY ENDOVASCULAR FEATURES

(71) Applicant: LightLab Imaging, Inc., Westford, MA (US)

(72) Inventors: Ajay Gopinath, Bedford, MA (US); Desmond Adler, Bedford, MA (US)

(73) Assignee: LightLab Imaging, Inc., Westford, MA (US)

( * ) Notice: Subject to any disclaimer, the term of this patent is extended or adjusted under 35 U.S.C. 154(b) by 18 days.

This patent is subject to a terminal disclaimer.

(21) Appl. No.: 17/084,805

(22) Filed: Oct. 30, 2020

(65) Prior Publication Data

US 2021/0082121 A1  Mar. 18, 2021

Related U.S. Application Data

(63) Continuation of application No. 15/948,084, filed on Apr. 9, 2018, now Pat. No. 10,878,572, which is a
(Continued)

(51) Int. Cl.
*A61B 5/02* (2006.01)
*A61B 6/00* (2006.01)
(Continued)

(52) U.S. Cl.
CPC .............. *G06T 7/13* (2017.01); *A61B 5/0066* (2013.01); *A61B 5/02007* (2013.01); *G06T 5/50* (2013.01);
(Continued)

(58) Field of Classification Search
None
See application file for complete search history.

(56) References Cited

U.S. PATENT DOCUMENTS

| 5,054,492 A | 10/1991 | Scribner et al. |
| 5,321,501 A | 6/1994 | Swanson et al. |

(Continued)

FOREIGN PATENT DOCUMENTS

| CN | 103462590 A | 12/2013 |
| CN | 104055540 A | 9/2014 |

(Continued)

OTHER PUBLICATIONS

Chinese Search Report for Application No. 201580073588.0 dated Nov. 2, 2020, 1 page.
(Continued)

*Primary Examiner* — Soo Shin
(74) *Attorney, Agent, or Firm* — Lerner, David, Littenberg, Krumholz & Mentlik, LLP

(57) ABSTRACT

In part, the disclosure relates to method for identifying regions of interest in a blood vessel. The method includes the steps of: providing OCT image data of the blood vessel; applying a plurality of different edge detection filters to the OCT image data to generate a filter response for each edge detection filter; identifying in each edge detection filter response any response maxima; combining the response maxima for each edge detection filter response while maintaining the spatial relationship of the response maxima, to thereby create edge filtered OCT data; and analyzing the edge filtered OCT data to identify a region of interest, the region of interest defined as a local cluster of response maxima. In one embodiment, one or more indicia are positioned in one or more panels to emphasize a reference vessel profile as part of a user interface.

32 Claims, 17 Drawing Sheets

Related U.S. Application Data continuation of application No. 14/968,729, filed on Dec. 14, 2015, now Pat. No. 9,940,723.

(60) Provisional application No. 62/153,816, filed on Apr. 28, 2015, provisional application No. 62/091,236, filed on Dec. 12, 2014.

(51) Int. Cl.

| | |
|---|---|
| *G06T 11/60* | (2006.01) |
| *G06T 19/20* | (2011.01) |
| *G06T 5/50* | (2006.01) |
| *G06T 7/12* | (2017.01) |
| *G06T 7/13* | (2017.01) |
| *A61B 5/00* | (2006.01) |
| *A61B 1/00* | (2006.01) |

(52) U.S. Cl.
CPC ............... *G06T 7/12* (2017.01); *G06T 11/60* (2013.01); *G06T 19/20* (2013.01); *A61B 1/00172* (2013.01); *A61B 5/0084* (2013.01); *A61B 6/504* (2013.01); *A61B 6/5217* (2013.01); *G06T 2200/08* (2013.01); *G06T 2207/10101* (2013.01); *G06T 2207/20104* (2013.01); *G06T 2207/20224* (2013.01); *G06T 2207/30101* (2013.01); *G06T 2210/41* (2013.01); *G06T 2211/404* (2013.01); *G06T 2219/2012* (2013.01)

(56) References Cited

U.S. PATENT DOCUMENTS

| | | |
|---|---|---|
| 5,459,570 A | 10/1995 | Swanson et al. |
| 5,465,147 A | 11/1995 | Swanson |
| 5,488,674 A | 1/1996 | Burt et al. |
| 5,509,093 A | 4/1996 | Miller et al. |
| 5,531,227 A | 7/1996 | Schneider |
| 5,619,368 A | 4/1997 | Swanson |
| 5,662,109 A | 9/1997 | Hutson |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,881,171 A | 3/1999 | Kinjo |
| 5,920,390 A | 7/1999 | Farahi et al. |
| 5,965,355 A | 10/1999 | Swanson et al. |
| 5,989,189 A | 11/1999 | LeBlanc et al. |
| 5,999,588 A | 12/1999 | Shao et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,208,883 B1 | 3/2001 | Holupka et al. |
| 6,282,011 B1 | 8/2001 | Tearney et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,608,717 B1 | 8/2003 | Medford et al. |
| 6,706,004 B2 | 3/2004 | Tearney et al. |
| 6,879,851 B2 | 4/2005 | McNamara et al. |
| 6,891,984 B2 | 5/2005 | Petersen et al. |
| 7,061,622 B2 | 6/2006 | Rollins et al. |
| 7,148,970 B2 | 12/2006 | de Boer |
| 7,208,333 B2 | 4/2007 | Flanders et al. |
| 7,231,243 B2 | 6/2007 | Tearney et al. |
| 7,241,286 B2 | 7/2007 | Atlas |
| 7,414,779 B2 | 8/2008 | Huber et al. |
| 7,415,049 B2 | 8/2008 | Flanders et al. |
| 7,477,768 B2 * | 1/2009 | Kaufman ............... G06T 7/136 |
| | | 382/128 |
| 7,593,559 B2 | 9/2009 | Toth et al. |
| 7,625,366 B2 | 12/2009 | Atlas |
| 7,729,746 B2 | 6/2010 | Redel et al. |
| 7,787,129 B2 | 8/2010 | Zysk et al. |
| 7,813,609 B2 | 10/2010 | Petersen et al. |
| 7,848,791 B2 | 12/2010 | Schmitt et al. |
| 7,916,387 B2 | 3/2011 | Schmitt |
| 7,935,060 B2 | 5/2011 | Schmitt et al. |
| 8,116,605 B2 | 2/2012 | Petersen et al. |
| 8,206,377 B2 | 6/2012 | Petroff |
| 8,325,419 B2 | 12/2012 | Schmitt |
| 8,358,461 B2 | 1/2013 | Huber et al. |
| 8,412,312 B2 | 4/2013 | Judell et al. |
| 8,449,468 B2 | 5/2013 | Petersen et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,687,201 B2 | 4/2014 | Adler |
| 8,786,336 B1 | 7/2014 | Schmitt |
| 8,831,321 B1 | 9/2014 | Elbasiony |
| 8,948,228 B2 | 2/2015 | Adler |
| 8,953,911 B1 | 2/2015 | Xu et al. |
| 8,983,580 B2 | 3/2015 | Boppart et al. |
| 9,610,064 B2 * | 4/2017 | Adler ................ A61B 5/6852 |
| 9,940,723 B2 * | 4/2018 | Gopinath ............... G06T 7/13 |
| 10,878,572 B2 | 12/2020 | Gopinath et al. |
| 11,166,668 B2 * | 11/2021 | Gopinath ............... A61B 5/742 |
| 2002/0115931 A1 | 8/2002 | Strauss et al. |
| 2002/0161351 A1 | 10/2002 | Samson et al. |
| 2003/0028100 A1 * | 2/2003 | Tearney ............ G01B 9/02072 |
| | | 600/431 |
| 2003/0179911 A1 | 9/2003 | Ho et al. |
| 2005/0201662 A1 | 9/2005 | Petersen et al. |
| 2005/0238067 A1 | 10/2005 | Choi |
| 2006/0095065 A1 | 5/2006 | Tanimura et al. |
| 2006/0104516 A1 * | 5/2006 | Lee ..................... G06T 7/181 |
| | | 382/199 |
| 2006/0165270 A1 | 7/2006 | Borgert et al. |
| 2006/0203859 A1 | 9/2006 | Cable et al. |
| 2006/0241461 A1 | 10/2006 | White |
| 2006/0241465 A1 | 10/2006 | Huennekens et al. |
| 2006/0244973 A1 | 11/2006 | Yun et al. |
| 2007/0081236 A1 | 4/2007 | Tearney |
| 2008/0008369 A1 * | 1/2008 | Koptenko ............. G06V 10/44 |
| | | 382/199 |
| 2008/0100612 A1 | 5/2008 | Dastmalchi et al. |
| 2008/0177183 A1 | 7/2008 | Courtney et al. |
| 2009/0079993 A1 | 3/2009 | Yatagai et al. |
| 2009/0174931 A1 | 7/2009 | Huber et al. |
| 2009/0306520 A1 | 12/2009 | Schmitt et al. |
| 2010/0076320 A1 | 3/2010 | Petersen et al. |
| 2011/0071404 A1 | 3/2011 | Schmitt et al. |
| 2011/0101207 A1 | 5/2011 | Schmitt |
| 2011/0157686 A1 | 6/2011 | Huber et al. |
| 2011/0190586 A1 | 8/2011 | Kemp |
| 2011/0228280 A1 | 9/2011 | Schmitt et al. |
| 2012/0013722 A1 | 1/2012 | Wong et al. |
| 2012/0075638 A1 * | 3/2012 | Rollins .............. G01B 9/02091 |
| | | 356/479 |
| 2012/0238869 A1 | 9/2012 | Schmitt et al. |
| 2012/0250028 A1 | 10/2012 | Schmitt et al. |
| 2012/0310081 A1 | 12/2012 | Adler et al. |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0310698 A1 | 11/2013 | Judell et al. |
| 2014/0018669 A1 * | 1/2014 | Xu ..................... G06K 9/6267 |
| | | 600/424 |
| 2014/0024931 A1 | 1/2014 | Winston et al. |
| 2014/0055791 A1 | 2/2014 | Iwase et al. |
| 2014/0094697 A1 | 4/2014 | Petroff et al. |

(56) References Cited

U.S. PATENT DOCUMENTS

| | | |
|---|---|---|
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0276011 A1 | 9/2014 | Schmitt et al. |
| 2014/0309536 A1 | 10/2014 | Douk et al. |
| 2014/0379269 A1 | 12/2014 | Schmitt |
| 2015/0119707 A1 | 4/2015 | Schmitt |
| 2015/0153157 A1 | 6/2015 | Schmitt et al. |
| 2015/0192405 A1 | 7/2015 | Schmitt |

FOREIGN PATENT DOCUMENTS

| | | |
|---|---|---|
| JP | H09138471 A | 5/1997 |
| JP | 2000003452 A | 1/2000 |
| JP | 2008004123 A | 1/2008 |
| JP | 2010179043 A | 8/2010 |
| JP | 2011521747 A | 7/2011 |
| JP | 2011173976 A | 9/2011 |
| JP | 2014042650 A | 3/2014 |
| WO | 2004066824 A2 | 8/2004 |
| WO | 2006024015 A1 | 3/2006 |
| WO | 2006076409 A2 | 7/2006 |
| WO | 2007002685 A2 | 1/2007 |
| WO | 2007028531 A1 | 3/2007 |
| WO | 2009149131 A1 | 12/2009 |
| WO | 2014002067 A2 | 1/2014 |
| WO | 2014055923 A2 | 4/2014 |
| WO | 2014175853 A1 | 10/2014 |

OTHER PUBLICATIONS

De Cock et al., "Development of 3D IVOCT Imaging and Co-Registration of IVOCT and Angiography in the Catherization Laboratory", Curr Cardiovasc Imaging Rep (2014) 7:9290 (14 pages).

Francesco Prati et al., "Expert review document on methodology, terminology, and clinical applications of optical coherence tomography: physical principles, methodology of image acquisition, and clinical application for assessment of coronaryarteries and atherosclerosis", European Heart Journal (2010), vol. 31, No. 4, pp. 401-415.

Gatenby, "Neural Networks, Part 1: Feedforward Hardlimited Networks", 2002, http://www.hpcc.org/datafile!V21 N1/neural1.html (8 pages).

International Search Report and Written Opinion from PCT/US2015/065626 dated May 27, 2016 (17 pages).

Japanese Office Action for Patent Application No. 2011-511907 dated Sep. 24, 2013 (9 pages).

Karanasos et al., "Optical Coherence Tomography: Potential Clinical Applications", Curr Cardiovasc Imaging Rep (2012) 5:206-220.

Kholodnykh et al., "Accurate Measurement of Total Attenuation Coefficient of Thin tissue with Optical Coherence Tomography", IEEE Journal of Selected Topics in Quantum Electronics, vol. 9, No. 2, Mar. 2003, pp. 210-221.

Notice of Reasons for Refusal for Japanese Application No. 2017550097 dated Jun. 2, 2020; 2 pages.

Notification of Transmittal of the International Search Report and the Written Opinion of the International Searching Authority for International Patent Application No. PCT/US2009/046035, dated Aug. 24, 2009, 15 pages.

Prati et al., "Expert review document part 2: methodology, terminology and clinical applications of optical coherence tomography for the assessment of interventional procedures", European Heart Journal (2012), http://eurheartj.oxfordjournals.org/content/early/2012/05/29/eurheartj.ehs095.full.pdf+htmal, (10 pages).

Schmitt et al., "Optical Coherence tomography of a dense tissue: statistics of attenuation and backscattering", Phys. Med. Biol. 39, Oct. 1994 , No. 10, pp. 1705-1720.

Van der Meer et al., "Localized Measurement of Optical Attenuation Coefficients of Atherosclerotic Plaque Constituents by Quantitative Optical Coherence Tomography", IEEE Transactions on Medical imaging, 24:10 (2005) pp. 1369-1376.

Xu et al., "Characterization of atherosclerosis plaques by measuring both backscattering and attenuation coefficients in optical coherence tomography", Journal of Biomedical Optics, vol. 13(3), May/Jun. 2008, 8 pages.

Extended European Search Report including Written Opinion for EP20217154.2 dated May 25, 2021; 8 pages.

* cited by examiner

SYSTEMS AND METHODS TO DETECT AND DISPLAY ENDOVASCULAR FEATURES

REFERENCE TO RELATED APPLICATIONS

This application is a continuation of U.S. patent application Ser. No. 15/948,084, filed on Apr. 9, 2018 which is a continuation of U.S. patent application Ser. No. 14/968,729, filed on Dec. 14, 2015, now U.S. Pat. No. 9,940,723, which claims priority from U.S. Provisional Application No. 62/091,236, filed on Dec. 12, 2014, and U.S. Provisional Application No. 62/153,816, filed on Apr. 28, 2015, the disclosures of which are incorporated by reference herein in their entirety.

FIELD

The disclosure relates in part to methods for detecting features and regions of interest such as calcified regions in blood vessels and for displaying those regions to a user.

BACKGROUND

Interventional cardiologists incorporate a variety of diagnostic tools during catheterization procedures in order to plan, guide, and assess therapies. Fluoroscopy is generally used to perform angiographic imaging of blood vessels. In turn, such blood vessel imaging is used by physicians to diagnose, locate and treat blood vessel disease during interventions such as bypass surgery or stent placement. Intravascular imaging technologies such as optical coherence tomography (OCT) are also valuable tools that can be used in lieu of or in combination with fluoroscopy to obtain high-resolution data regarding the condition of the blood vessels for a given subject.

Intravascular optical coherence tomography is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. The level of detail made possible with OCT allows a user to diagnose as well as monitor the progression of coronary artery disease.

Calcium plaques in blood vessels are a major cause of heart disease. Calcium deposition results in a narrowing of blood vessel diameter and also stiffens the blood vessel wall, which significantly reduces blood vessel performance. Calcium plaques therefore are one of the major targets of cardiovascular intervention but remain difficult to detect in OCT images.

The present disclosure addresses the need for enhanced detection methods for automatically identifying calcified regions within endovascular tissue.

SUMMARY

The disclosure is based in part on the discovery that calcified regions of endovascular tissue exhibit characteristic patterns in intravascular images such as optical coherence tomography (OCT) images. Calcified regions appear as discrete, darkened shapes against the brighter vascular tissue background of OCT images. Moreover, calcified regions are bounded by prominent edges on one or more sides or, in one embodiment, all sides. These patterns can be used to differentiate calcified tissue from other endoluminal features (e.g., lipid plaques and normal thickening) using automated computer programs trained to detect edges. In addition, data from many OCT frames can be combined and into a graphic user interface dashboard that assists users with rapid disease diagnosis and treatment planning.

In one embodiment, OCT image data are processed using a plurality of edge detection filters (e.g., outer, inner, left, and/or right edge filters). Calcified regions have prominent edges and respond to both vertical and horizontal edge detection filters, whereas lipid plaques and normal stenoses typically respond only to horizontal edge detection filters. The line will extend left to right to left—high intensity transitioning to low intensity. Thus, vertical edge detection (e.g., left and right edges) can be used to differentiate calcium plaques from other plaque types. In addition, filter responses from multiple neighboring frames can be combined to resolve large calcium deposits, which may not be resolvable from a single OCT frame.

In part, the disclosure relates to a method for identifying regions of interest in a blood vessel. The method includes the steps of: providing OCT image data of the blood vessel; applying a plurality of different edge detection filters to the OCT image data to generate a filter response for each edge detection filter; identifying in each edge detection filter response any response maxima, the local response maxima representing detected edges;

combining the response maxima for each edge detection filter response while maintaining the spatial relationship of the response maxima, to thereby create edge filtered OCT data; and analyzing the edge filtered OCT data to identify a region of interest, the region of interest defined as a local cluster of response maxima. In one embodiment, a relative extremum is used in lieu of response maxima.

In one embodiment, the edge detection filters are based on Gaussian derivatives. In one embodiment, the OCT image data is formatted in polar space or comprises a polar image. In one embodiment, the OCT image data is formatted in Cartesian space or comprises a cross-sectional image. In one embodiment, the plurality of different edge detection filters includes a horizontal edge detection filter and a vertical edge detection filter. In one embodiment, the horizontal edge detection filter comprises a top edge filter and a bottom edge filter.

In one embodiment, the vertical edge detection filter comprises a left edge detection filter and a right edge detection filter. In one embodiment, the method includes the step of: repeating steps for a plurality of OCT image frames. In one embodiment, the method includes the step of: rendering a two- or three-dimensional model of the blood vessel using the plurality of OCT image frames, based on the OCT edge filtered data and the regions of interest. In one embodiment, the local maxima are determined by comparing filter responses to a predetermined threshold. In one embodiment, the plurality of filters comprises at least a top edge filter, a left edge filter, and a right edge filter.

In one embodiment, the method includes the step of: identifying the region of interest as a calcified region if the region of interest includes at least one vertical edge response maxima. In one embodiment, method includes the step of: identifying the region of interest as a non-calcified region if the region of interest includes no vertical edge response maxima. In one embodiment, the model is a three-dimensional longitudinal rendering of the blood vessel, the model including a graphic for indicating the arc length of the region of interest, the graphic includes a ring coaxial with the blood vessel with the blood vessel extending through the ring, the ring having a first colored portion proportional to the arc length of healthy tissue and a second colored portion proportional to the arc length of the region of interest. In one embodiment, in lieu of first colored portion and a second colored portion a first and second indicia are used which may include color, shapes, and other graphical elements or overlays.

In part, the disclosure relates to a system for identifying regions of interest in a blood vessel, the system includes: a processor in communication with a memory, the memory containing instructions that when executed cause the processor to: obtain OCT image data of the blood vessel; apply a plurality of different edge detection filters to the OCT image data to generate a filter response for each filter; identify in each filter response any response maxima, the local response maxima representing detected edges; combine the response maxima for each filter response while maintaining the spatial relationship of the response maxima, to thereby create edge filtered OCT data; and analyze the edge filtered OCT data to identify a region of interest, the region of interest defined as a local cluster of response maxima containing OCT image data. In one embodiment, the OCT image data is a plurality of scan lines. In one embodiment, the OCT image data is a polar image.

In part, one embodiment of the disclosure relates to an intravascular data collection system and one or more software-based graphic user interfaces and software modules to perform one or more detection and display processes as described herein. In one embodiment, intravascular data is collected while angiography data is simultaneously collected. In one embodiment, the disclosure relates to the display of information relating to a calcified portion of a blood vessel relative to one or more of angiography image or an optical coherence tomography image (or other intravascular image). In one embodiment, the disclosure relates to the display of information relating to a bioresorbable vascular scaffold (BVS) or bioresorbable scaffolds (BRS) in a blood vessel relative to one or more of angiography image or an optical coherence tomography image (or other intravascular image). In one embodiment, the disclosure relates to the display of information relating to a bioresorbable vascular scaffold (BVS) or bioresorbable scaffolds (BRS) to help guide the expansion of the BRS/BVS.

BRIEF DESCRIPTION OF DRAWINGS

The figures are not necessarily to scale, emphasis instead generally being placed upon illustrative principles. The figures are to be considered illustrative in all respects.

FIG. 2A is an outer edge filter that detects high (top) to low (bottom) horizontal edges. FIG. 2B is an inner edge filter that detects low (top) to high (bottom) horizontal edges. FIG. 2C is a left edge filter that detects high (left) to low (right) vertical edges. FIG. 2D is a right edge filter that detects low (left) to high (right) vertical edges.

FIG. 3A is an outer edge detection response. FIG. 3B is an inner edge detection response. FIG. 3C is a left edge detection response. FIG. 3D is a right edge detection response.

FIGS. 6A-C are neighboring frames showing a calcified region. FIGS. 6B and D are discrimination frames compare nonplaque data showing non-calcified tissue controls.

FIG. 15A graphically depicts the arc length of a calcium deposit. FIG. 15B is a stylized graphic depicting lumen diameter along the pullback zone.

FIG. 16A graphically depicts the arc length of a calcium deposit. FIG. 16B is a stylized graphic depicting lumen diameter along the pullback zone.

DETAILED DESCRIPTION

Figure 1A:
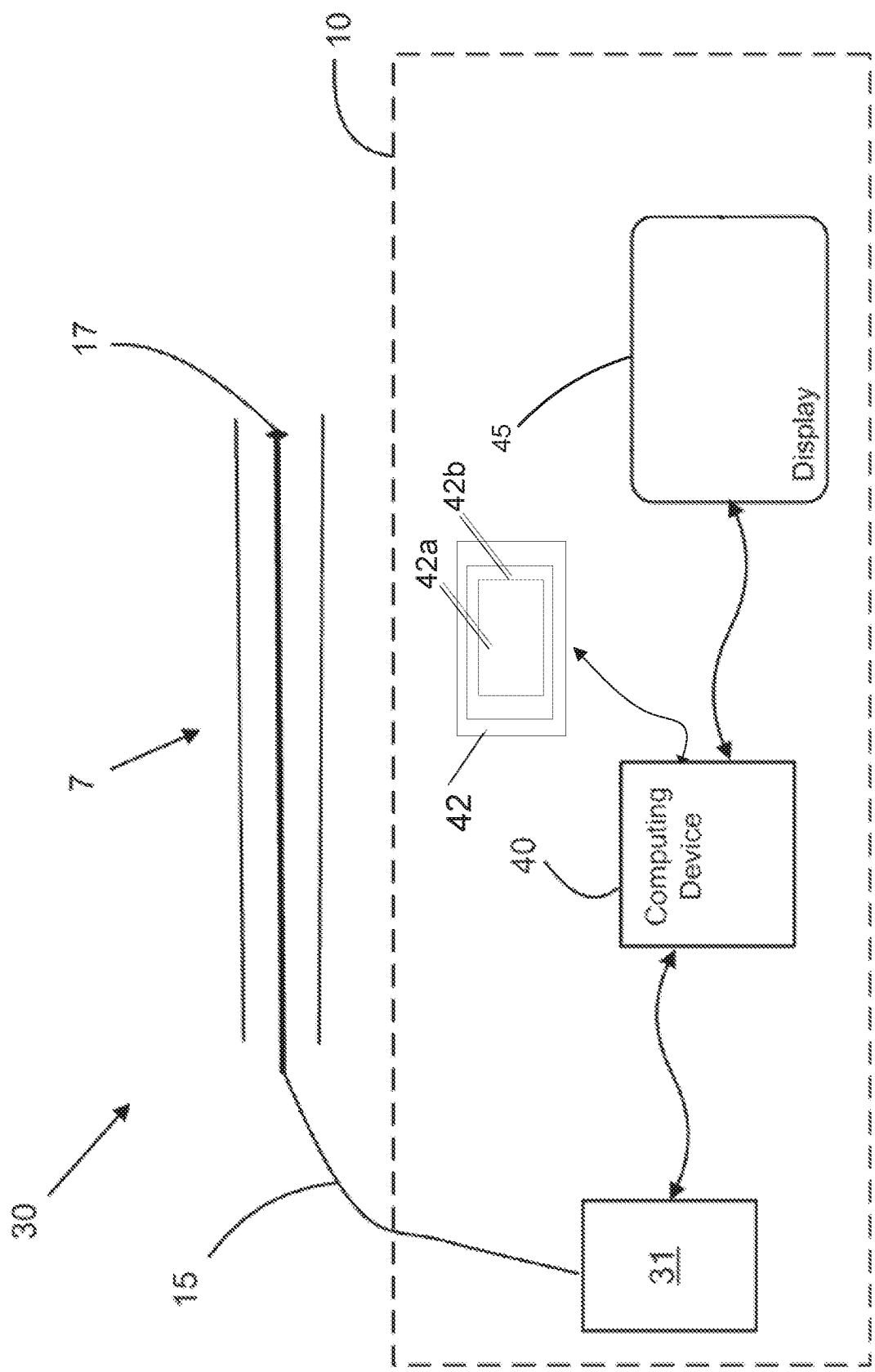
FIG. 1A shows a schematic diagram of an intravascular imaging and data collection system.

Intravascular optical coherence tomography (OCT) images provide high-resolution visualization of coronary artery morphology. In part, the disclosure relates to the automatic detection and/or classification of intracoronary plaques (calcium, lipid, fibrosis, and thrombus). Inner and outer calcified boundaries are also detected and displayed in one embodiment. The process of detection and classification can enhance the interpretation of OCT images and provide targeted information to diagnosticians. In part, the disclosure relates to systems and methods for displaying the results of data analysis applied to an intravascular data set to the user in a way that is clear, easy to interpret, and conducive to diagnosing a subject. In part, this disclosure describes a graphic user interface (GUI) that provides user interface and graphic data representations that can be applied to one or more plaque types and other regions or conditions of a given blood vessel of interest. In one embodiment, a calcified region is referred to by CR in the specification and in the figures.

In part, the disclosure relates to a data collection system such as an intravascular data collection system suitable for use in cath lab such as an optical coherence tomography system. In part, the disclosure relates to a data collection system that includes a processor suitable for displaying intravascular image data. The image data displayed includes data or images generated based upon depth measurements. In one embodiment, the image data is generated using optical coherence tomography. The system can also display a user interface for display of intravascular information such as data relating to intravascular plaques.

Calcified regions have distinct edges in OCT images and calcified regions appear as discrete, darkened shapes against the brighter vascular tissue background. The contrast between calcified tissue and surrounding healthy tissue permits automated edge detection using directional edge filters. Calcified regions can be detected in as few as one OCT image frames, but more typically are detected by filtering multiple neighboring OCT frames and combining the filter data into a two or three dimensional rendering of the blood vessel. Improved user interfaces also are disclosed for demarcating calcified regions in two and three dimensional renderings.

Optical coherence tomography (OCT) is an imaging modality that uses an interferometer to obtain distance measurements relative to a sample such as, for example, a blood vessel or objects disposed therein. A blood vessel can be imaged using an intravascular data collection probe. A guidewire can be used to introduce the probe into the blood vessel.

The data collection probe can be disposed in and pulled back along a length of a blood vessel while collecting data. A torque wire can be part of the probe and can encircle a light transmission and receiving path such as an optical fiber. The torque wire can be used to rotate the probe. As the optical fiber is retracted (pulled-back) along the length of the vessel, a plurality of scans or OCT data sets are collected as the probe or a portion thereof rotates. This is referred to as a pullback in one embodiment. These data sets can be used to identify regions of interest such as a stenosis or physiological indicia of a stenosis. The data sets can be used to identify calcified regions, stents, and other features in a blood vessel as described in more detail herein. The display related features described herein with regard to calcified regions can also be used relative to stents and other detectable and displayable intravascular features.

In one embodiment, the data collection probe is an OCT probe configured for use with an OCT system that includes an interferometer and a data processing system. A light source such as a swept source laser can be in optical communication with the interferometer and transmit light to a sample arm and a reference arm of the interferometer. The distance measurements collected using the OCT probe can be processed to generate frames of image data such as cross-sectional views or longitudinal views (L-mode views) of the blood vessel. These images can be processed using one or more image data processing steps or other methods or steps as described herein. The data processing system can include one or more processors and one or more memory storage devices. The data processing system can generate a plurality of edge detection filters suitable for application to a polar image generated using intravascular data such as OCT or ultrasound data.

As shown in FIG. 1A, a data collection system 30 for use in collecting intravascular data includes a data collection probe 17 that can be used to image a blood vessel. A guidewire can be used to introduce the probe 17 into the blood vessel. The data collection probe 17 can be introduced and pulled back along a length of a blood vessel 7 while collecting data. As the probe is retracted (pulled-back) along a length of the vessel, a plurality of scans or OCT data sets are collected as the probe or a portion thereof rotates. These data sets, or collections of frames of image data, can be used to identify regions of interest such as a calcified region.

In one embodiment, the data collection probe 17 is an OCT probe configured for use with an OCT system 10 that includes an interferometer and a data processing system. The distance measurements collected using the OCT probe 17 can be processed to generate frames of image data such as cross-sectional views or longitudinal views (L-mode views) of the blood vessel. For clarity, a cross-sectional view can include without limitation a longitudinal view. These images can be processed using one or more image data processing modules or stages.

The probe 17 is in optical communication with an OCT system 10. The OCT system or subsystem 10 that connects to probe 17 via an optical fiber 15 can include a light source such as a laser, an interferometer having a sample arm and a reference arm, various optical paths, a clock generator, photodiodes, and other OCT system components.

In one embodiment, an optical receiver 31, such as a balanced photodiode based system, can receive light collected by the probe 17. A computing device 40 such as a computer, processor, ASIC, or other device can be part of the OCT system 10 or can be included as a separate subsystem in electrical or optical communication with the OCT system 10. The computing device 40 can include memory, storage, buses and other components suitable for processing data and software such as image data processing stages configured for feature (e.g. calcification) detection, analysis, and visualization.

In one embodiment, the computing device 40 includes or accesses software modules 42 or programs, such as a plaque (e.g., a calcium plaque) detection module 42a, a display module, and other software modules 42b, such as stent detection or other detection and display modules. For example, the computing device 40 can access a calcification detection module for detecting the existence of a calcium plaque in a blood vessel. The software can also include or be in communication with user interface software components to toggle views on and off and to display and toggle the various user interface display modes such as stent planning, fly through and other viewing modes. The software modules or programs can include an image data processing pipeline or component modules thereof and one or more graphical user interfaces (GUI). An exemplary image processing pipeline is used for transforming collected OCT data into two dimensional and three dimensional views of blood vessels and stents and calcified regions. The image data processing pipeline or any of the methods described herein are stored in memory and executed using one or more computing devices such as a processor, device, or other integrated circuit.

As shown in FIG. 1A, a display 45 can also be part of the system 10 for showing information such as cross-sectional and longitudinal views of a blood vessel generated using collected OCT data. System 10 can be used to display image data relating to one or more calcifications detected in the blood vessel. In one embodiment, one or more steps can be performed automatically or without user input other than initial user input to navigate relative to one or more images, enter information, select or interact with an input such as a controller or user interface component, or otherwise indicate one or more system outputs. In one embodiment, a calcium plaque view is presented as an option to select to facilitate review of a two or three-dimensional view of a representation of the vessel and one or more calcium plaques. Toggling between one or more viewing modes in response to user inputs can be performed relative to various steps described herein. A similar view can also be used to display stent information.

The OCT-based information can be displayed using one or more graphic user interface(s) (GUI). In addition, this information can include, without limitation, cross-sectional scan data, longitudinal scans, diameter graphs, image masks, lumen border, plaque sizes, plaque circumference, visual indicia of plaque location, and other images or representations of a blood vessel or the underlying distance measurements obtained using an OCT system and data collection probe.

The computing device 40 can also include software or programs, which can be stored in one or more memory devices, configured to identify calcium plaques and other blood vessel features such as with text, arrows, color coding, highlighting, contour lines, or other suitable human or machine readable indicia.

The display 45 depicts various views of the blood vessel, in accordance with an embodiment. The display can include a menu for showing or hiding various features, such as a menu for selecting blood vessel features to display, and a menu for selecting the virtual camera angle of the display. The user can toggle between multiple view angles on the user display. In addition, the user can toggle between different side branches on the user display, such as by selecting particular side branches and/or by selecting a view associated with a particular side branch. In one embodiment, the image processing pipeline and associated software modules detect the lumen boundary and calcium plaques imaged using the data collected during a pullback.

Once the OCT data is obtained with a probe and stored in memory; it can be processed to generate information such as a cross-sectional, a longitudinal, and/or a three-dimensional view of the blood vessel along the length of the pullback region or a subset thereof. These views can be depicted as part of a user interface as shown, for example, in FIGS. 13-16. The images of the blood vessel generated using the distances measurements obtained from the OCT system provide information about the blood vessel.

Accordingly, in part, the disclosure relates to software-based methods and related systems and devices suitable for evaluating and depicting information regarding a blood vessel or other vascular information of interest. The OCT data can be used to generate 2-D views such as cross-sectional and longitudinal views of a blood vessel before or after an initial stent deployment or corrective stent related procedure. The OCT data obtained using a data collection probe and various data processing software modules can be used to identify, characterize, and visualize a stent and/or one or more properties relating to the stent and/or the lumen in which it is disposed.

Figure 1B:
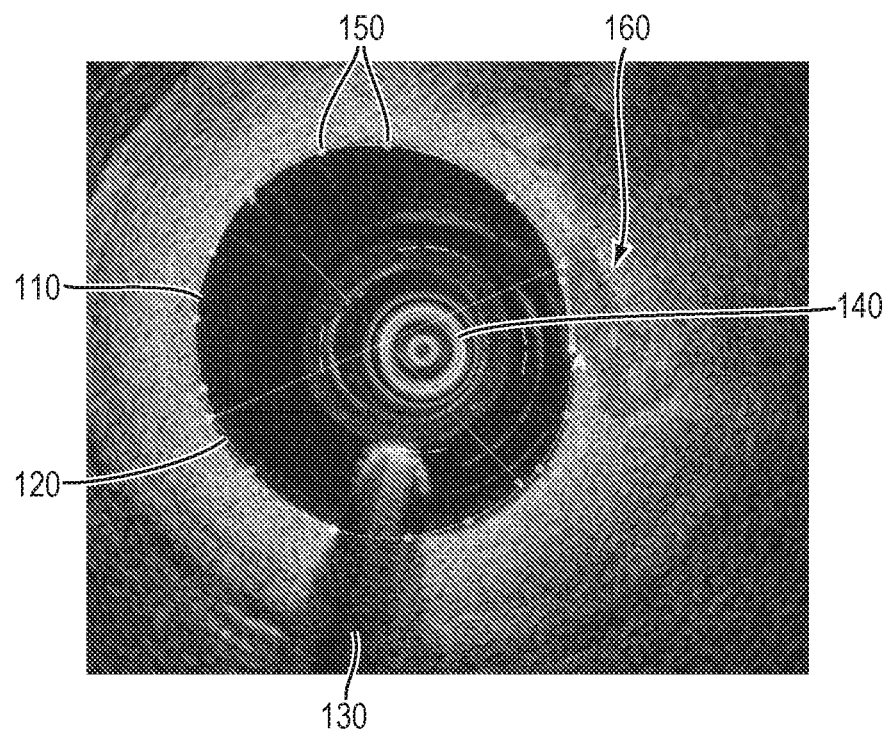
FIG. 1B is a cross-sectional OCT image frame of an arterial blood vessel.

FIG. 1B is a cross-sectional OCT image frame of an arterial blood vessel. The dark circular shadow in the center of the image is the vessel lumen 110. The vessel lumen is surrounded by a blood vessel wall 120. The OCT catheter guidewire leaves a shadow 130 that obscures part of the of OCT image. Backscattering markers on the OCT catheter sheath create a series of concentric rings 140 in the center of the vessel lumen to assist in orienting the image and demarcating the direction of the lumen. Markers 150 are added to delineate the lumen boundary.

With continued reference to FIG. 1B, a calcified region or calcium plaque 160 is clearly visible as a discrete, darkened region in the blood vessel wall on the right side of the image. The edges of the calcified region are prominent. The calcified region extends radially from the surface of the blood vessel wall, where most calcifications initiate, into the vessel wall. Although an arterial blood vessel is shown, the methods, devices, and systems disclosed herein also can be used to detect calcified regions in other blood vessels such as venous blood vessels.

Figure 1C:
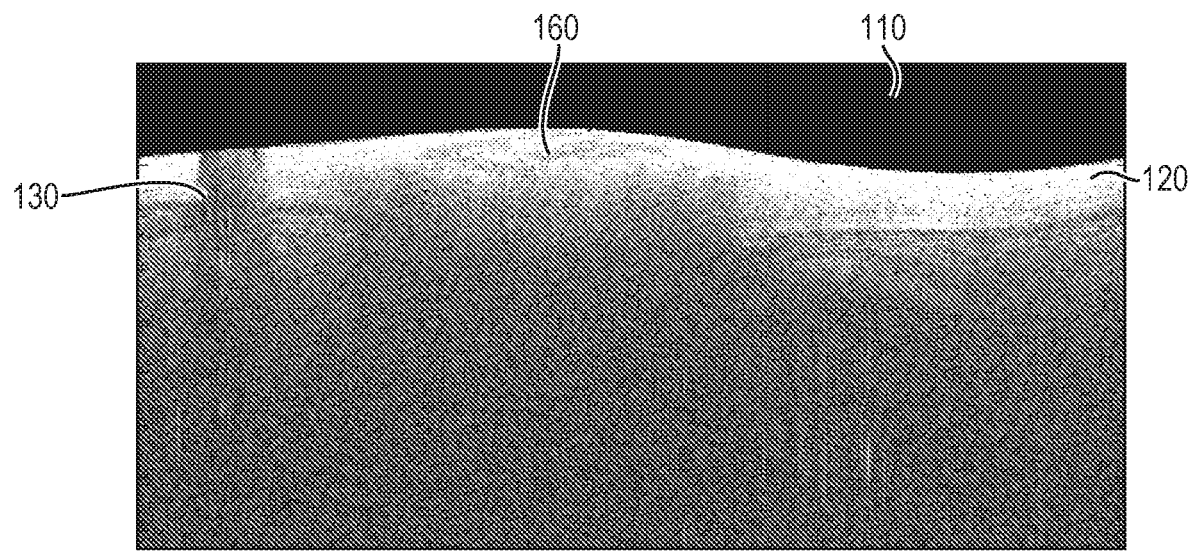
FIG. 1C is the OCT image frame from FIG. 1A shown in polar space. The x-axis is angle and the y-axis is depth.

FIG. 1C shows the collected scan lines obtained using the data collection probe in polar coordinate space. The OCT image frame from FIG. 1B is a cross-sectional view generated from the scan lines shown in the polar image of FIG. 1C. The OCT image frame can be generated directly from the collected OCT data. In all polar images depicted herein, the x-axis is angular measurements and the y-axis is distance measurements. Depth corresponds to the radial thickness of the vessel wall. In FIG. 1C, the lumen 110 is at the top of the image and the vessel wall 120 is at the bottom of the image. The guidewire shadow 130 appears on the left. The calcified region 160 is visible in the center of the image near the lumen.

In various embodiments, calcified regions are detected automatically by processing OCT images with edge detection filters. FIGS. 2A-D show four exemplary edge detection filters. Each filter detects a different boundary direction. In one embodiment, the edge detection filters include a top bottom filter, a bottom top filter, a right left filter and a left right filter. Other directional orientations indicating a transition from a first direction to a second direction can be use without limitation. Intensity changes such as from low to high can also be use to categorize the filters or otherwise specify their respective filter responses. In one embodiment, these directional edge detectors give maximum response or a relative extrema response in regions where the edge lines up with the direction of the ridge.

Figure 2B:
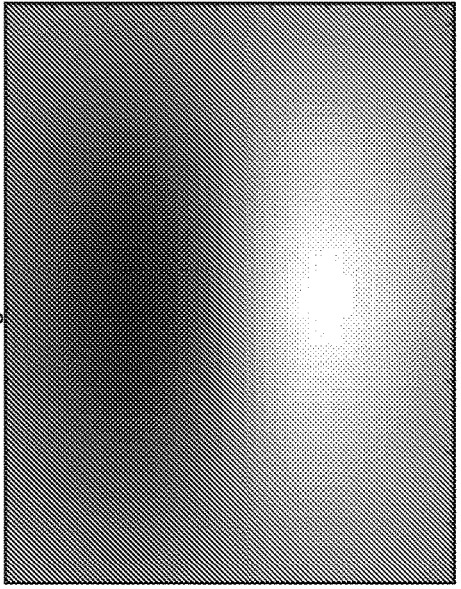
FIGS. 2A-D are edge detection filters.
Figure 2D:
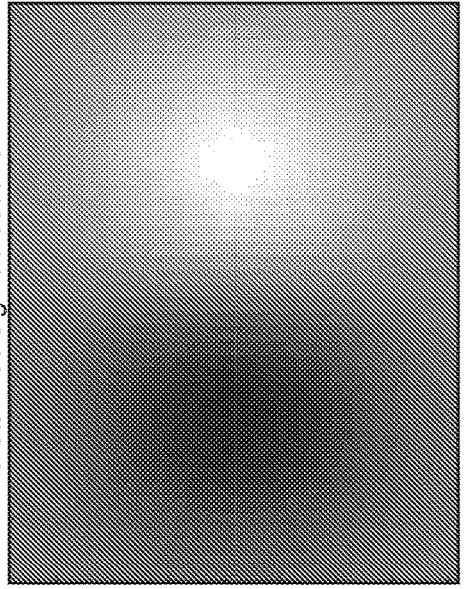
Figure 2A:
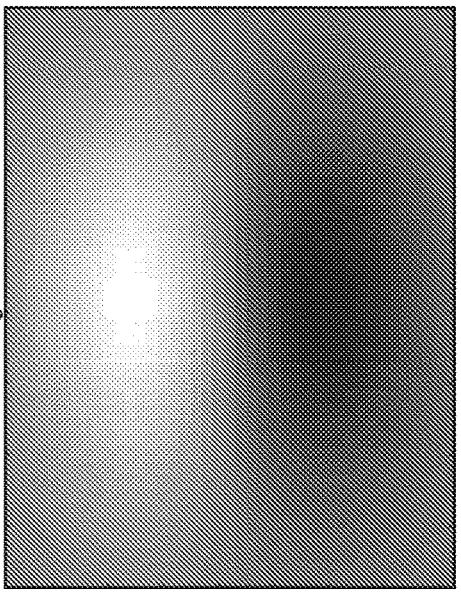
Figure 2C:
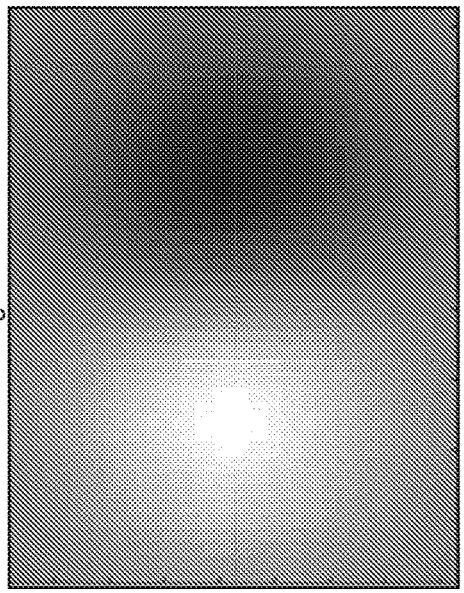

FIG. 2A is an outer edge filter that detects high (top) to low (bottom) horizontal edges. The outer edge filter could also be referred to as a top edge filter because polar space OCT images typically orient the endothelium at the top of the image. FIG. 2B is an inner edge filter that detects low (top) to high (bottom) horizontal edges. The inner edge filter could also be referred to as a bottom edge filter because polar space OCT images typically orient the intima tissue layer at the bottom of the image. FIG. 2C is a left edge filter that detects high (left) to low (right) vertical edges. FIG. 2D is a right edge filter that detects a low (left) to high (right) vertical edge.

In one embodiment, filters can be used that have an orientation such as a diagonal orientation or another orientation such as an angled orientation relative to an origin of the filter. In one embodiment, additional filters can be added having complementary and/or opposite orientations to provide additional data to improve boundary detection and/or increase confidence levels. In one embodiment, the filters can be implemented using one or more processors and instructions to generate a filter such as an operator or matrix to transform the collected OCT image data.

The terms "outer" and "inner" refer to the location of edges relative to the underlying vascular tissue, with outer edges being located closer to the endothelium and inner edges being located closer to underlying vascular smooth muscle. The inner and outer edges correspond to the radial depth or penetration of the calcified region. The terms "left"

and "right" refer to the relative location of edges in polar space images. The left and right edges correspond to the arc length, or width, of the calcified region in the blood vessel.

In one embodiment, the edge detection filters are based on Gaussian derivatives and are similar to the wavelet transform. These and other Gaussian or other edge detection filters can be used in various embodiments.

OCT polar image frames are processed using one or more edge detection filters. For example, the outer edge detection filter in FIG. 2A detects horizontal edges that step from high to low signal intensity, which usually is the outer edge of the calcified region adjacent the vessel lumen. The inner edge detection filter in FIG. 2B detects edges that step from low to high signal intensity, which usually is the inner edge of the calcified region within the vessel wall. For large calcifications, the inner edge may not be visible in the OCT image.

Similarly, the left edge detection filter in FIG. 2C detects vertical edges that step from high to low signal intensity, which usually is the left edge of the calcified region. Finally, the right edge detection filter in FIG. 2D detects vertical edges that step from low to high signal intensity, which often is the right edge of the calcified region.

Preferably, OCT image data such as OCT polar images are filtered with at least the two horizontal edge detection filters because calcified regions respond to horizontal edge detection filters, whereas lipid plaques and normal features typically do not respond strongly to horizontal edge detection filters. Thus, horizontal edge detection permits differentiation of calcified regions from other vessel features, which is helpful for selecting treatment options, such as stent types. For example, calcified regions are comprised of stiffened tissue and therefore require more resilient stents that other types of stenoses.

In various embodiments, OCT image data are processed using a plurality of edge detection filters (e.g., outer, inner, left, and/or right edge filters). Preferably, at least two different edge detection filters are used, and more preferably at least three different edge detection filters are used, and most preferably four edge different edge detection filters are used. Calcified regions have prominent edges and respond to both vertical and horizontal edge detection filters, whereas lipid plaques and normal stenoses typically respond only to horizontal edge detection filters. Lipid plaques have a single gradient which corresponds to a single horizontal edge. Thus, vertical edge detection (e.g., left and right edges) can be used to differentiate calcium plaques from non-calcified tissue features. In addition, calcified regions show more and higher intensity filter responses than non-calcified regions.

Figure 3A:
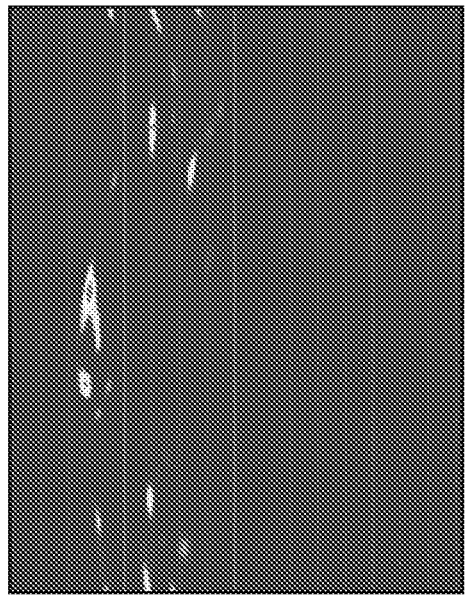
FIGS. 3A-D show responses of the directional edge filters shown in FIGS. 2A-D, respectively.
Figure 3B:
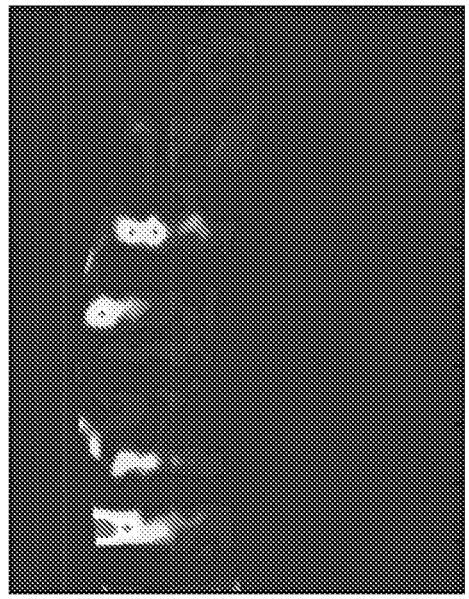
Figure 3C:
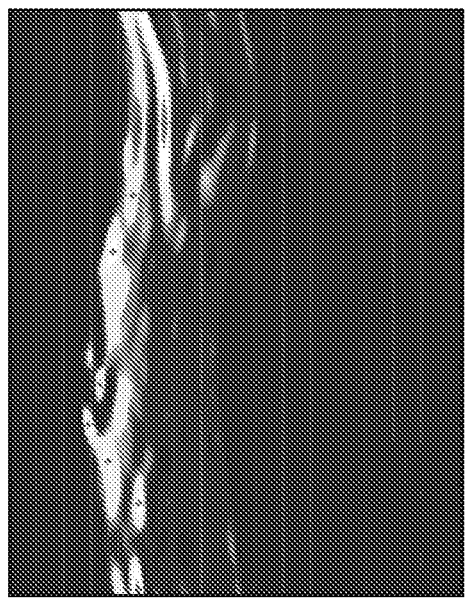
Figure 3D:
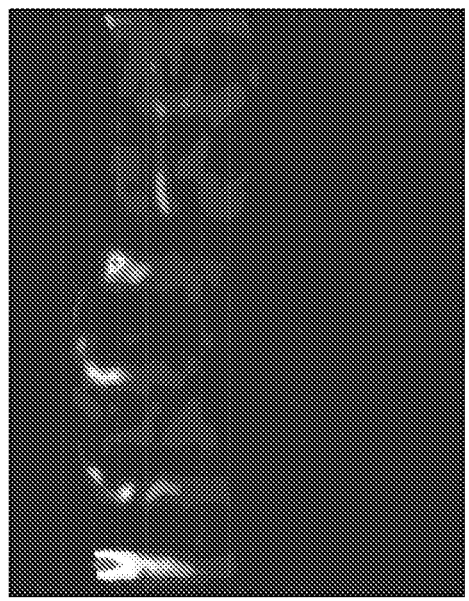

In an exemplary embodiment, the polar image shown in FIG. 1B is processed for edge detection. FIGS. 3A-D show responses of the directional edge filters shown in FIGS. 2A-D, respectively. FIG. 3A is a top horizontal edge detection response. FIG. 3B is a bottom horizontal edge detection response. FIG. 3C is a left vertical edge detection response. FIG. 3D is a right vertical edge detection response. Longer wavelengths, darker region, denote higher intensity filter responses and shorter wavelengths, lighter regions, indicate lower intensity filter responses. Asterisks indicate the local maxima of the response for each filter. In certain embodiments, responses exceeding a predetermined threshold are deemed local maxima.

Figure 4A:
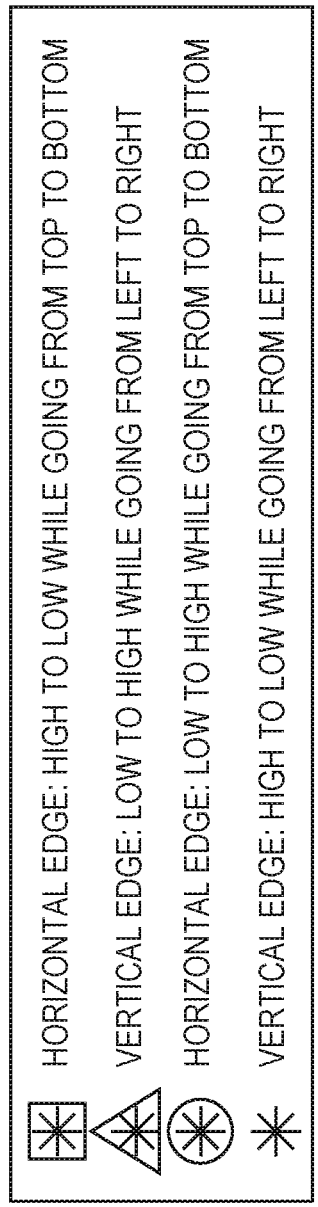
FIG. 4A is a legend for demarcating local maxima in edge detection responses.
Figure 4B:
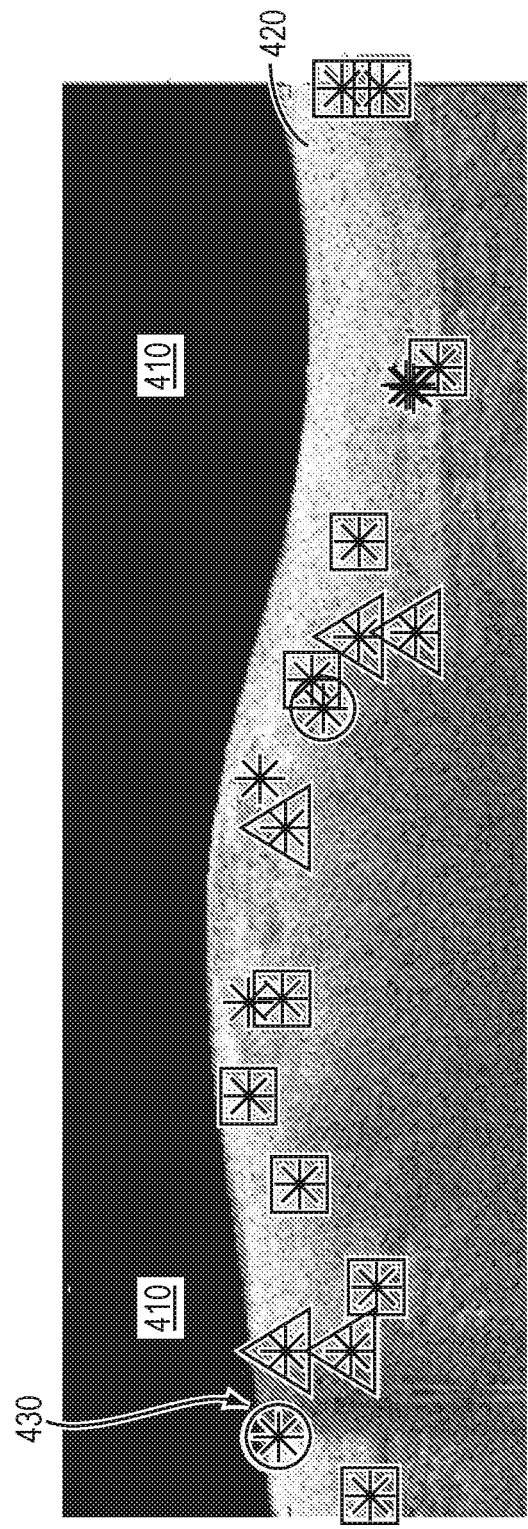
FIG. 4B is an OCT image frame shown in polar space with local maxima for each detection filter overlaid.

Referring to FIG. 4B, the local maxima of the filter responses (FIGS. 3A-D) are overlaid on a polar image to illustrate edge detection for the calcified region. FIG. 4A is a legend identifying the maxima for each directional edge filter. A cluster of local maxima responses from all four directional filters indicates a calcified region. The guidewire shadow 430 is clearly visible on the left side of the image. Maxima associated with the guidewire shadow are ignored as spurious. In FIG. 4B, the CA region is shown by region 420. The lumen of the blood vessel 410 is also visible as black in the edge detection filtered polar image of FIG. 4B.

Figure 5A:
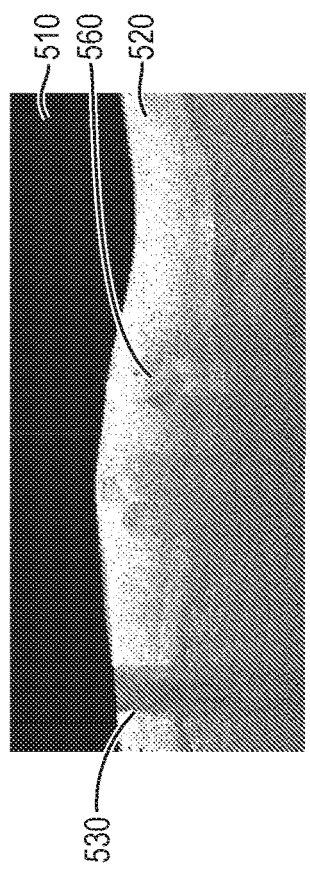
FIG. 5A is an OCT image frame shown in polar space of a small calcified region.
Figure 5C:
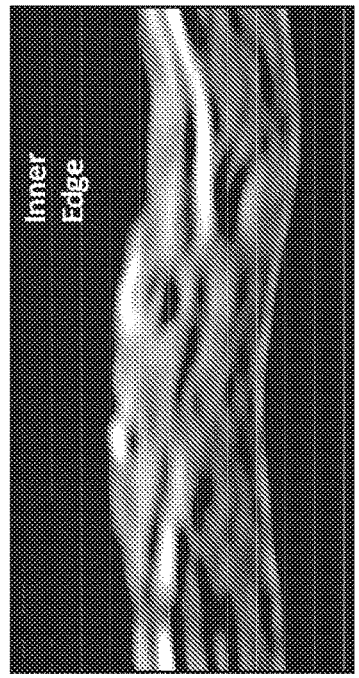
FIGS. 5B-E are filter responses in each direction for the image in FIG. 5A.
Figure 5E:
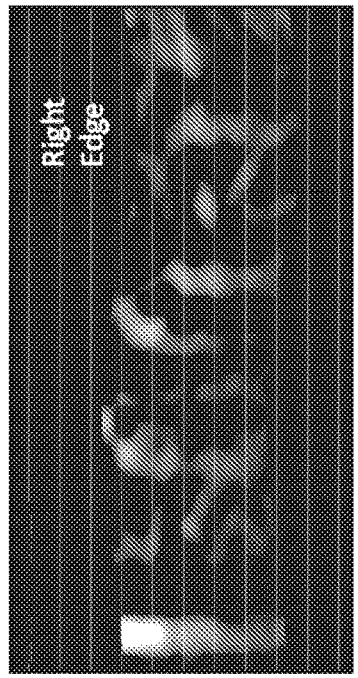
Figure 5B:
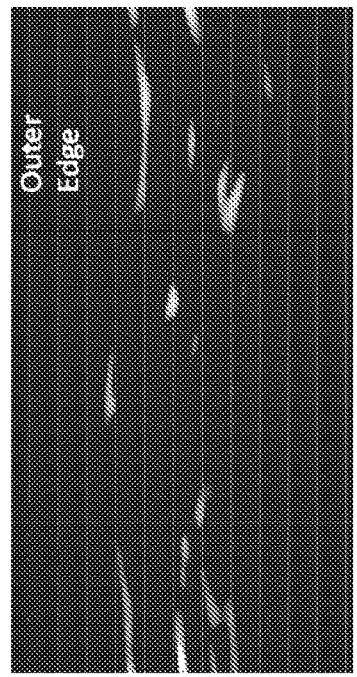
Figure 5D:
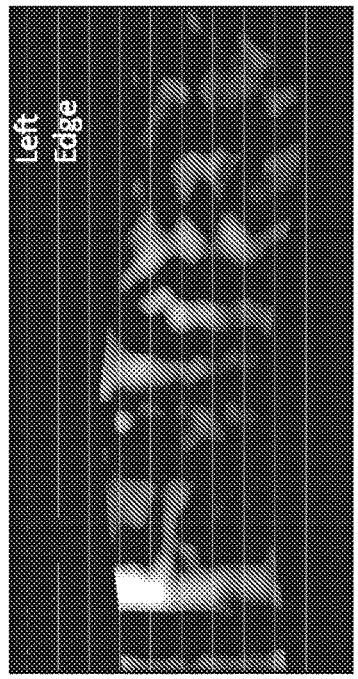

FIG. 5A is a polar image frame with a small calcified region 560 visible near the center of the image. The guidewire shadow 530 is visible on the left. The image shown in FIG. 5A is processed with all four edge detection filters to resolve the boundaries of the calcified region. FIGS. 5B-E are the filter responses: FIG. 5B is the outer edge horizontal filter, FIG. 5C is the inner edge horizontal filter, FIG. 5D is the left edge vertical filter, and FIG. 5E is the right edge vertical filter. Local maxima are marked with white asterisks.

Figure 6A:
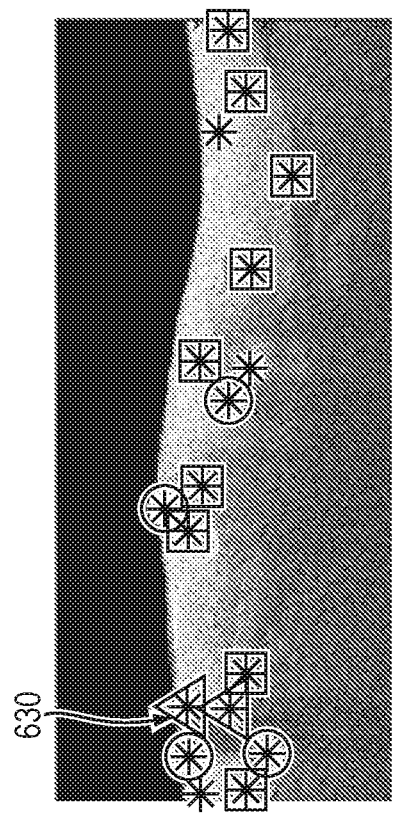
FIGS. 6A-D are OCT image frames shown in polar space.
Figure 6B:
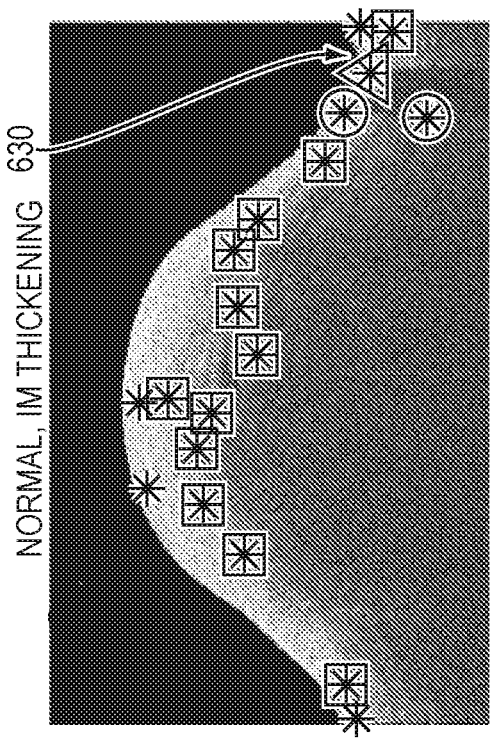

FIG. 6A shows the polar image (FIG. 5A) with the filter responses (FIGS. 5B-E) overlaid on polar image that includes sequence of scan lines in one embodiment. The filter response can be shown on different views of OCT data and scored to identify regions of interest in one embodiment. The top, bottom, and left edges of the calcified region were detected by filtering the polar image of FIG. 6A. Edge detecting or otherwise filtering of the neighboring frame (FIG. 6B) also detects three edges of the calcified region; however, the right edge is detected instead of the left edge. It may therefore be necessary to combine filter responses from multiple neighboring OCT frames to detect all boundaries of a calcified region. The use of cross-frame data and results can improve the accuracy of the detection of calcified regions in one embodiment.

Figure 6C:
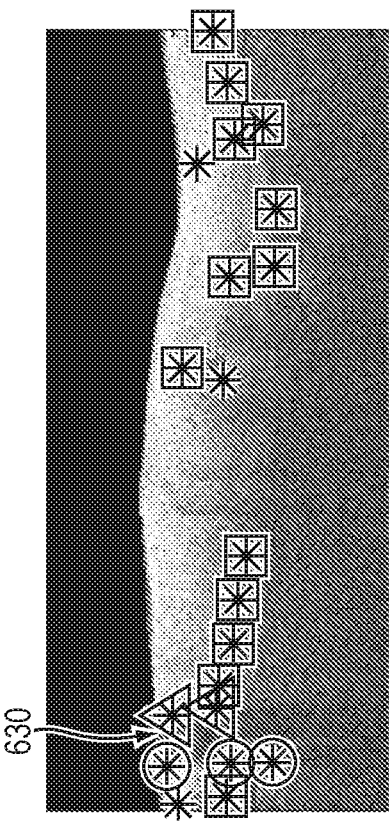
Figure 6D:
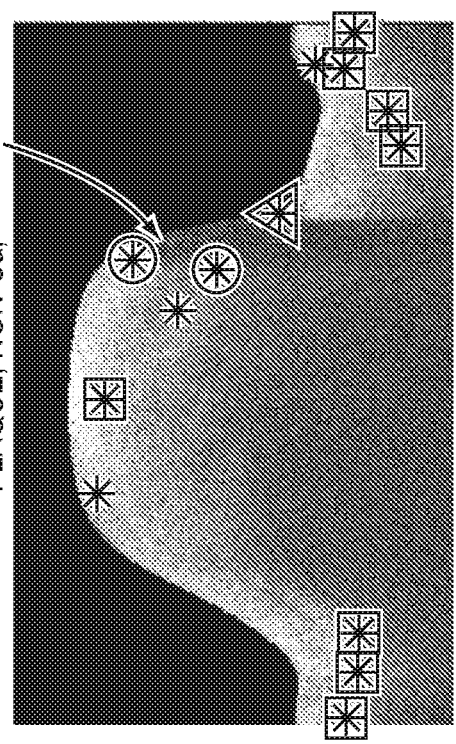

FIGS. 6C and 6D are controls showing endovascular regions exhibiting normal intima-media thicking and a non-calcified plaque, respectively. With normal intima media thickening (FIG. 6C), only horizontal edge maxima—inner and outer edges—are detected. Similarly, a non-calcified plaque (FIG. 6D) generates fewer maxima and no vertical edge maxima.

Figure 7A:
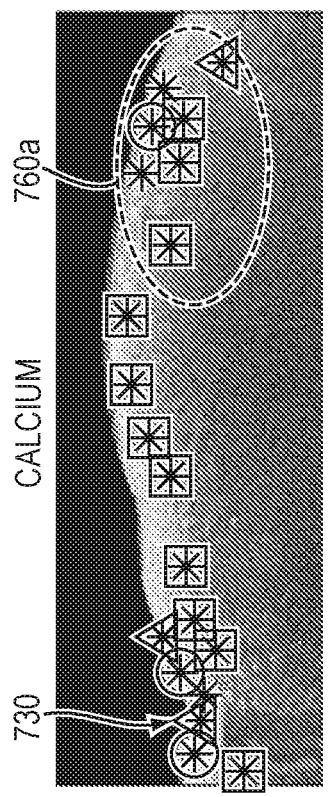
FIGS. 7A-C are neighboring OCT image frames shown in polar space of a calcified region.
Figure 7B:
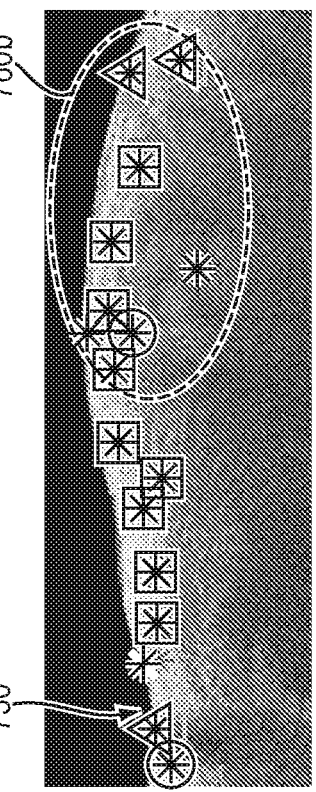
Figure 7C:
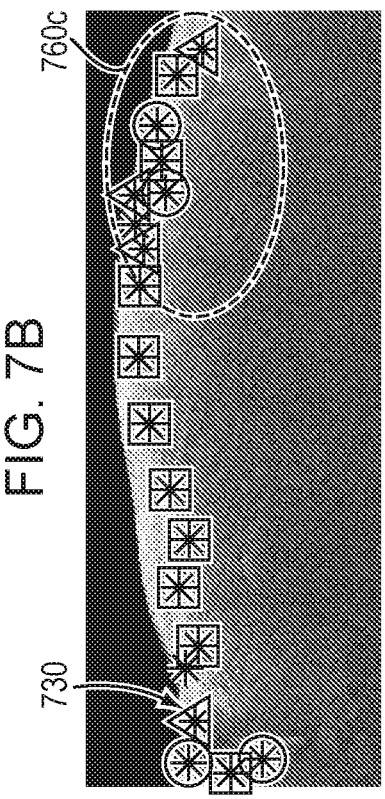
Figure 7D:
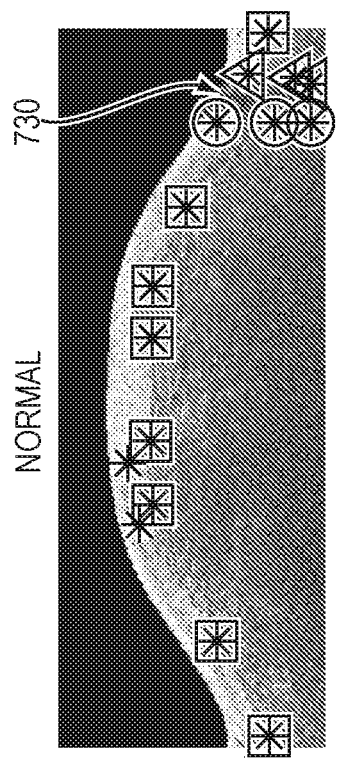
FIGS. 7D-F are neighboring OCT image frames shown in polar space of non-calcified tissue controls.
Figure 7E:
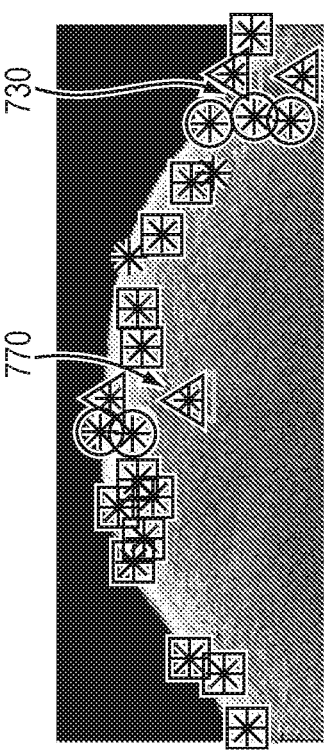
Figure 7F:
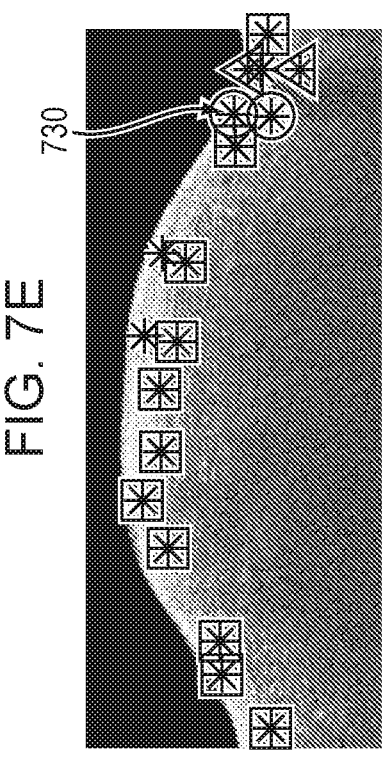

FIGS. 7A-F are further examples of filter overlays for calcified (FIGS. 7A-C) and normal (FIGS. 7D-F) endovascular tissues. FIGS. 7A-C are neighboring frames showing a calcified region 760a,b,c in successive frames. Maxima are present in each frame for all four filter directions. FIGS. 7D-F are neighboring frames showing normal tissue having a thickened intima-media. These images contain only inner and outer maxima. In FIG. 7E, the columnar feature 770 triggers vertical edge detection maxima. However, it is unlikely that this feature is a calcium plaque due to its regular, columnar shape, and also because calcified regions tend to have large, irregular surface areas. The feature 770 is likely a bubble or other feature that generates an imaging artifact.

Figure 8A:
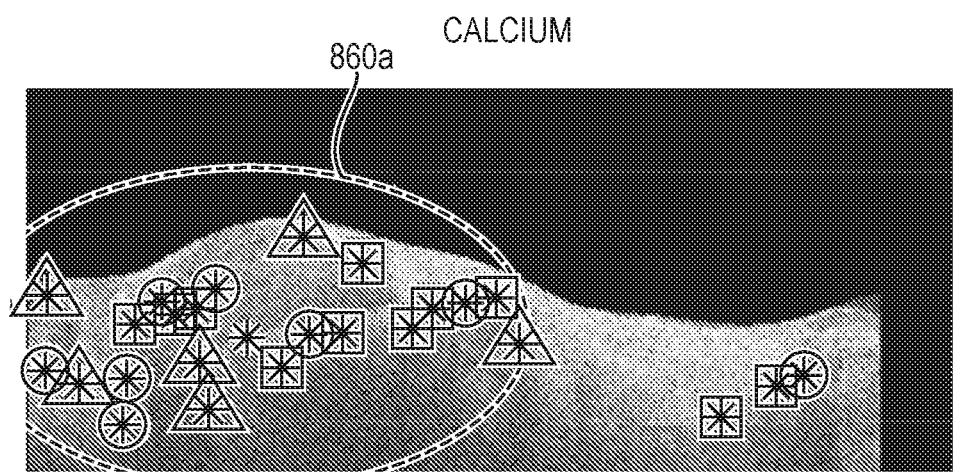
FIGS. 8A-C are OCT image frames shown in polar space of calcified regions.
Figure 8B:
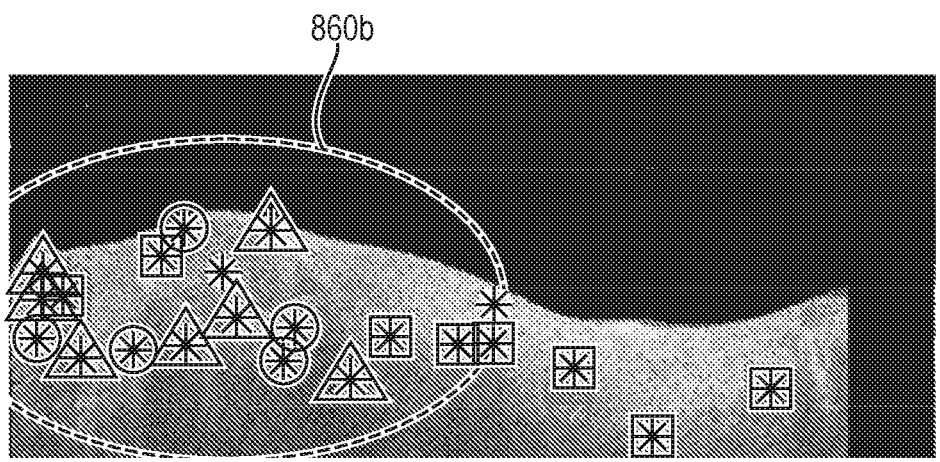
Figure 8C:
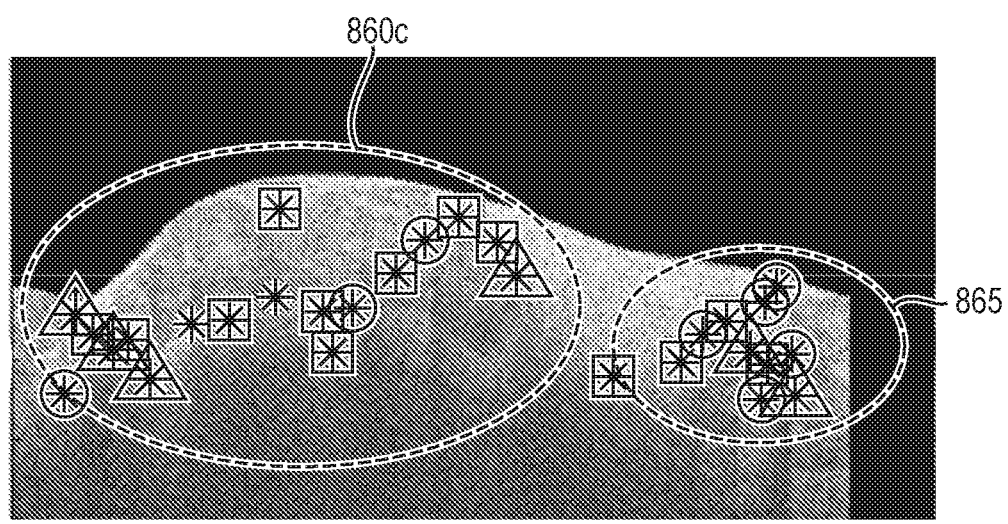
Figure 9A:
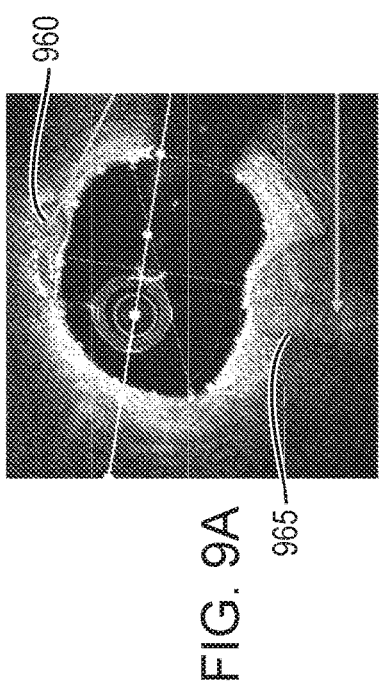
FIGS. 9A-9F are a composite of OCT cross-sectional images and polar images of a calcified region in a blood vessel.
Figure 9B:
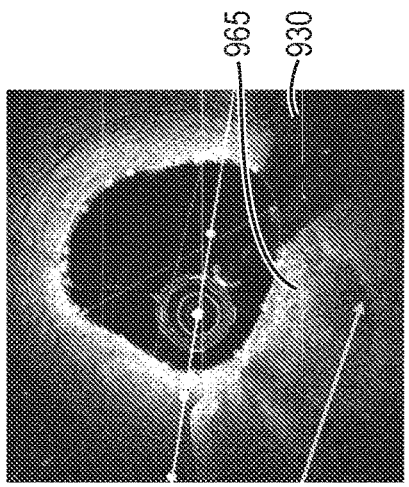
Figure 9C:
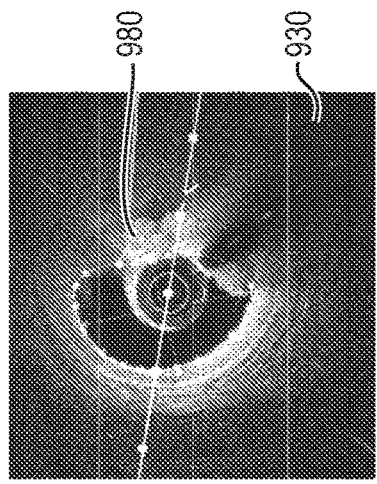
Figure 9D:
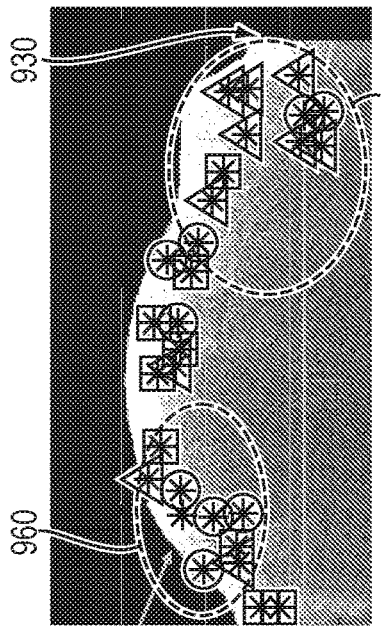
Figure 9E:
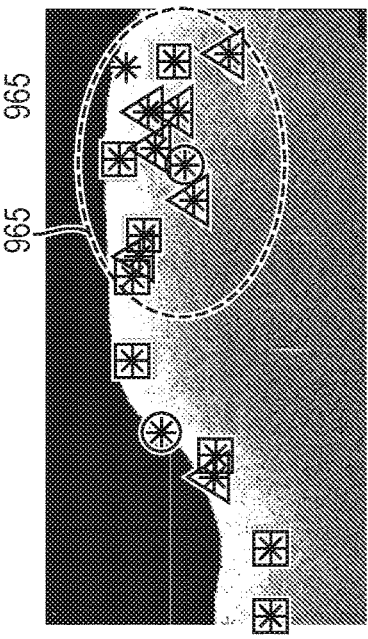
Figure 9F:
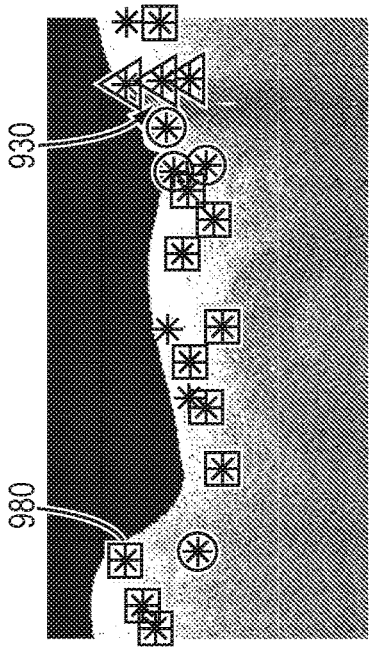

FIGS. 8A-C are neighboring frames showing a large calcified region 860a,b,c. The calcified region produces multiple maxima for all four directional filters in each frame. In addition a smaller calcified region 865 is visible on the right, which may be part of the same calcification. Although calcified region 865 lacks an inner edge maxima, the number and close clustering of edge maxima indicate that this likely is a calcification. If more filters with different orientations are used more responses will responses will result which will increase accuracy. Sometimes inner maxima are not detected if the calcification extends deeply into the vessel wall—e.g., deeper than the OCT scan. In some embodiments, filter responses from multiple neighboring OCT frames are combined to resolve large calcium deposits, which may not be resolvable from a single OCT frame. The guidewire shadow would appear on the right but has been redacted in the images.

FIG. 9 is a composite of OCT cross-sectional images and polar images of a calcified region in a blood vessel, further illustrating the disclosure. FIGS. 9A-C are cross-sectional images from the same neighborhood and FIGS. 9D-E are the corresponding polar images. A calcified region 960 visible at the top of FIG. 9A produces edge detection maxima in all four directions, as shown in FIG. 9D. A second calcified region 965 at the bottom of FIG. 9A produces edge detection maxima in three directions in response to a plurality of directional edge detection filters. The second calcified region 965 remains prominent in a later frame, FIGS. 9B and 9E. The second calcified region exceeds the depth of the OCT scan; therefore, no inner maxima are observed. Finally, FIGS. 9C and 9E show a natural stenosis 980 on the right side of the vessel. This stenosis can be ruled out as a calcified region because it generates few edge detection maxima and the maxima are in only two directions. The guidewire shadow 930 is evident, except in FIG. 9D, in which it has been redacted.

In various embodiments, a computer, processor or other system or device is programmed to filter successive OCT frames using a plurality of edge detection filters in order to identify clusters of local maxima or local extremum. The process flow shown in FIG. 9 of three polar images (FIGS. 9D, 9C, and 9F) processed with suitable edge detection filters to determine how many maxima are detected and with regard to which directions. The sufficiency of maximum and directions having such maxima can be used to identify calcified regions.

Calcified regions can be distinguished from non-calcified regions using vertical edge detection because non-calcified regions typically do not respond to vertical edge detection filters. In addition, the inner edge of large calcifications may be too deep to be resolved by a standard OCT scan. Thus, a cluster of at least outer, left, and right edge maxima in a given OCT frame define a region of interest (ROI) that corresponds to a calcified region. This ROI is derived by setting a bounding box on the cluster of filter responses that correspond to three, or preferably all four, directional filters.

The process of defining or determining a region of interest (ROI) uses several filter responses that originate from one or more tissue depths to indicate a depth of a calcium nodule. A bounding box, ellipse, sphere or other boundary that contains one or more of or all of a set of calcium filter responses can be used with the dimensions of the sphere, box, ellipse or other boundary to determine a back edge or other edge of a calcium nodule or region. Calcium acts like a hard region in a blood vessel relative to which compaction resulting from expanding a stent in the vicinity of such a calcified region is problematic.

As a result, identifying these regions is of interest. A region of interest can be found by generating a boundary around a region identified using filter responses and connecting the points of the boundary or finding a common point such as a centroid or other point and connecting with dots of boundary to obtain distance measurements between points. This process can be used to measure the depth of a calcified region.

Figure 10:
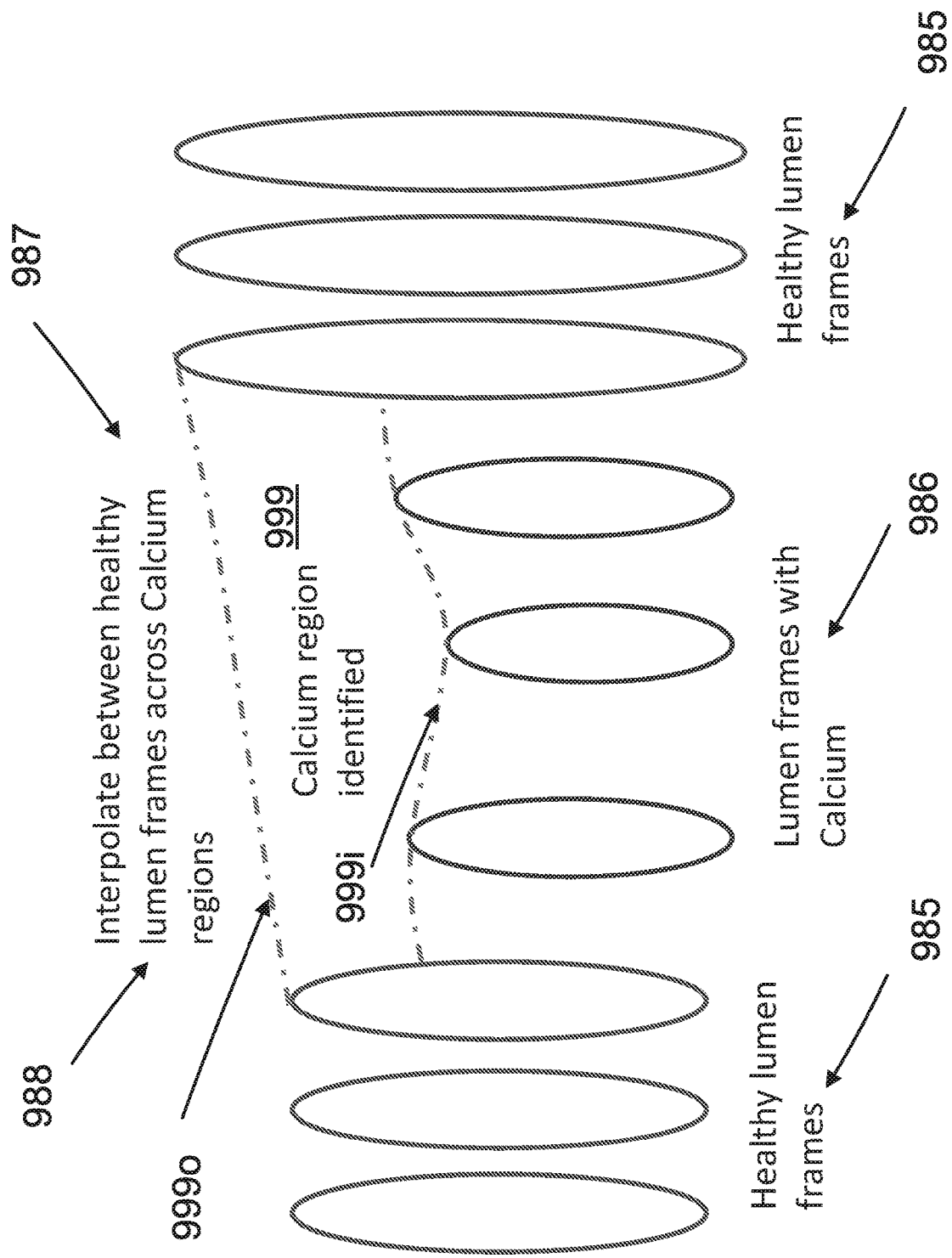
FIG. 10 is a schematic integrating data from multiple OCT frames.

The ROI of the filter responses can then be used to estimate the size and/or volume of calcified tissue in each OCT frame. These can be determined using a point fitting and measurement process relative to a given boundary selected to define the region of interest. In some embodiments, the ROIs do not define the exact boundaries of the calcified region but instead provide an estimate of the calcified region. After ROIs have been ascertained in one or more OCT frames, the frames are combined for user analysis in 3D volume rendering, 2D cross-sections, and longitudinal displays of the blood vessel. FIG. 10 is a schematic showing cross-frame information about lumen diameter for a section of blood vessel.

Exemplary processing steps or stages by which a CR is detected are also shown. The healthy lumen frames are detectable/displayable 985 on either side of the CR. The frames of lumen/tissue that include calcium 986 are in between the healthy frames. Three frames showing calcified stenosis are bounded to the left and to the right by three healthy (non-stenosed) lumen frames. The calcification reduces the diameter of the vessel by about 33%. This frame tracking of healthy and calcified region containing frames can be used to select regions in a vessel for stent placement. Interpolation between healthy lumen frames and CRs is performed to identify CRs 999. The calcium region 999 is identified and it is shown disposed between an outer boundary 999o and an inner boundary 999i.

Figure 11A:
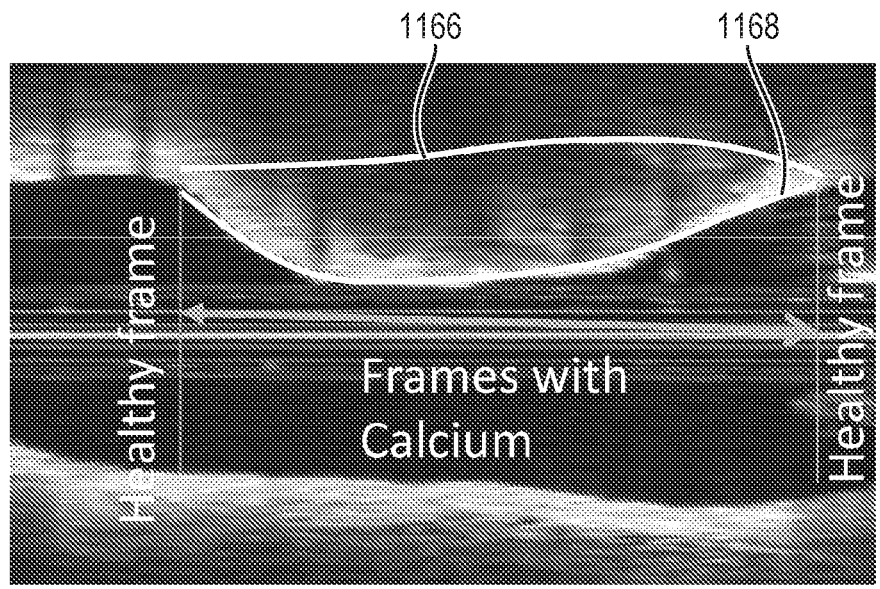
FIG. 11A is an L-Mode image showing a calcified region bounded by healthy regions.

In another embodiment, FIG. 11A is an L-Mode image showing a two dimensional longitudinal rendering of a calcified region bounded by healthy regions. Bold lines denote the inner 1166 and outer 1168 boundaries of the calcified region.

Figure 11B:
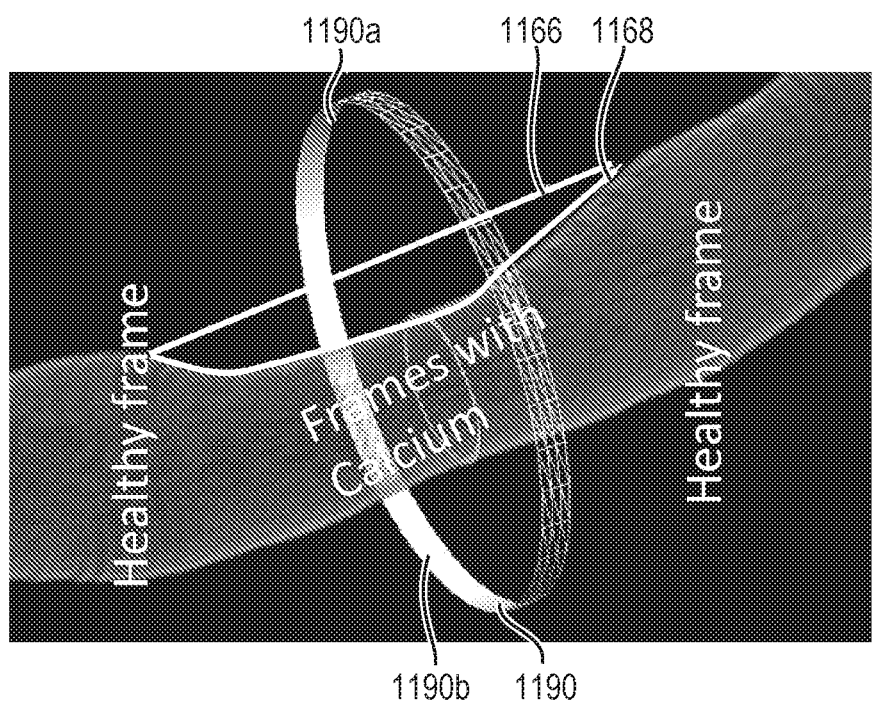
FIG. 11B is a three dimensional volume rendering of FIG. 11A.

In another embodiment, FIG. 11B is a three dimensional volume rendering of the same data shown in FIG. 11A, with the calcified region highlighted by bold lines. Bold lines denote the inner 1166 and outer 1168 boundaries of the calcified region. In addition, a circumferential marker 1190 provides a visual aid to assist the user in quickly evaluating the size of the calcification. The circumferential marker graphically depicts the arc length of the calcified region as a proportion of the vessel circumference. The arc length of the calcified region is demarcated by a first indicia (e.g., a first color and/or pattern) 1190a, and adjacent non-calcified tissue is demarcated by a second indicia (e.g., a second color and/or pattern) 1190b. As the marker shows, the calcified region extends about halfway around the vessel circumference.

Figure 12B:
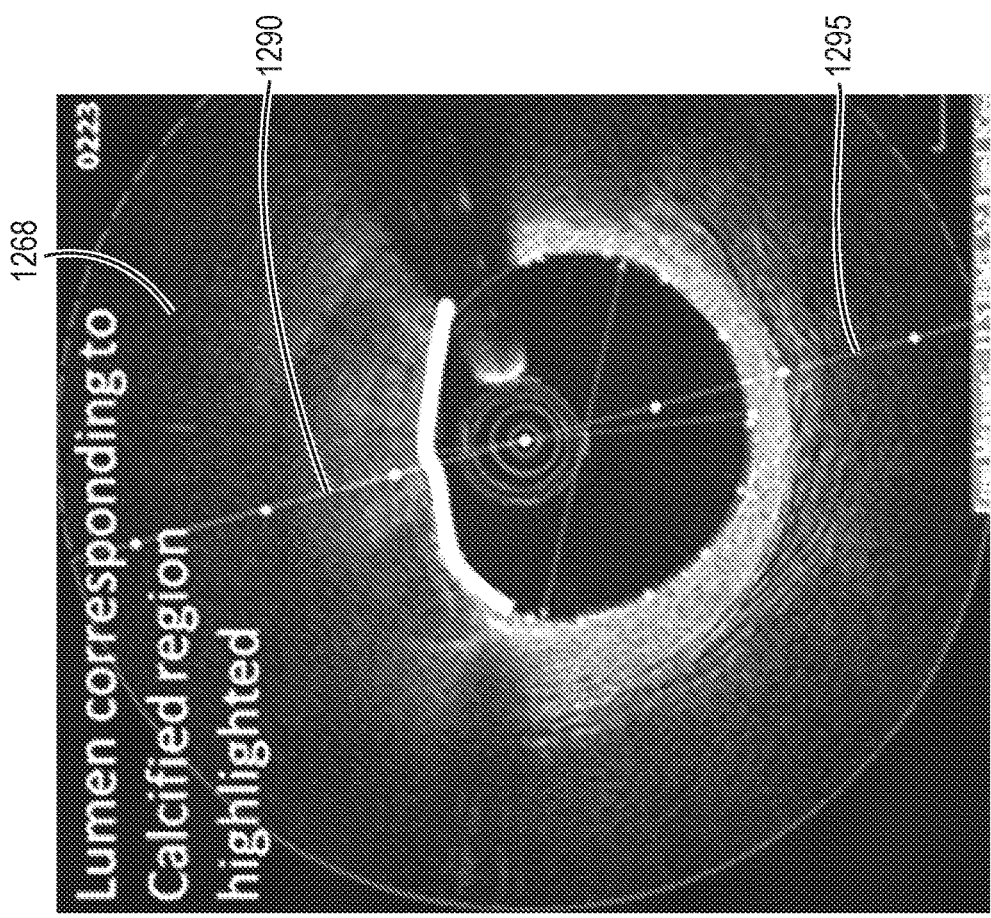
FIG. 12B is a cross-sectional OCT image with the inner boundary of the calcified region demarcated by a bold line.
Figure 12A:
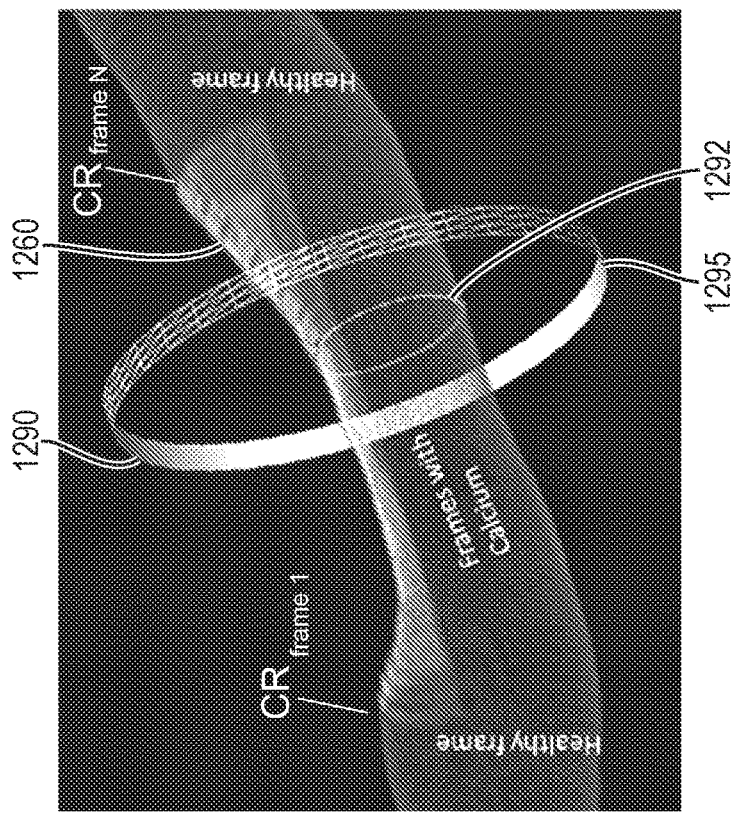
FIG. 12A is a three dimensional rendering of a vessel highlighting the calcified region.

FIG. 12A shows a three dimensional rendering of a vessel highlighting the inner boundary of the calcified region 1260 along the luminal surface. A positional marker 1292 can be added below the circumferential marker 1290 (top) and circumferential marker 1295 (bottom) to facilitate rapid image interpretation by a user. In FIG. 12B, the top and bottom portions of the circumferential marker 1290 and 1295 correspond to the upper line segment 1290 and the lower line segment 1295, respectively. The positional marker demarcates the precise cross-sectional area depicted by the circumferential marker. The circumferential marker and/or the positional marker can be movable and interactive such that the user can select different cross sections and/or different viewing perspectives.

In FIG. 12A, a first calcified region end frame and a second calcified region end frame are designated by CR frame 1 and CR frame N. Either of these frames can be considered as the start or end frame of the calcified region CR. In one embodiment, N can be 2 to indicate the second frame or N can be the number of frames in the CR. Thus, if a CR has 100 frames of image data the boundary frames can be CR frame 1 and CR frame 100.

In another embodiment, FIG. 12B a shows a cross-sectional image corresponding to the location of the positional marker shown in FIG. 12A. The outer edge of the calcification is demarcated by a bold line 1268 to assist the user in evaluating the stenosis.

Figure 13A:
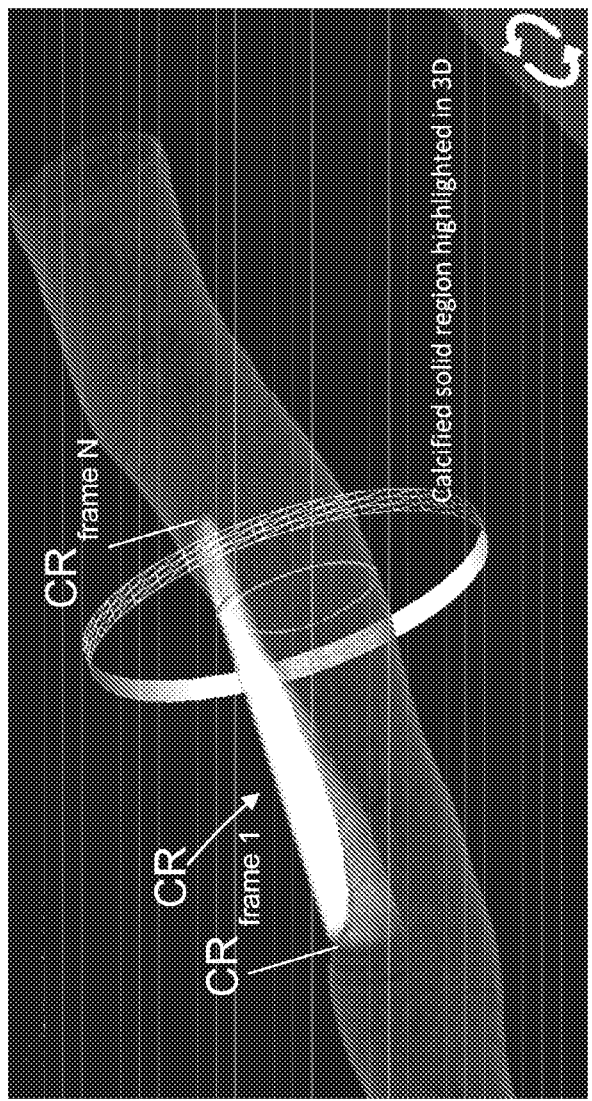
FIG. 13A is a three dimensional rendering of a vessel with the calcified region volume rendered.
Figure 13B:
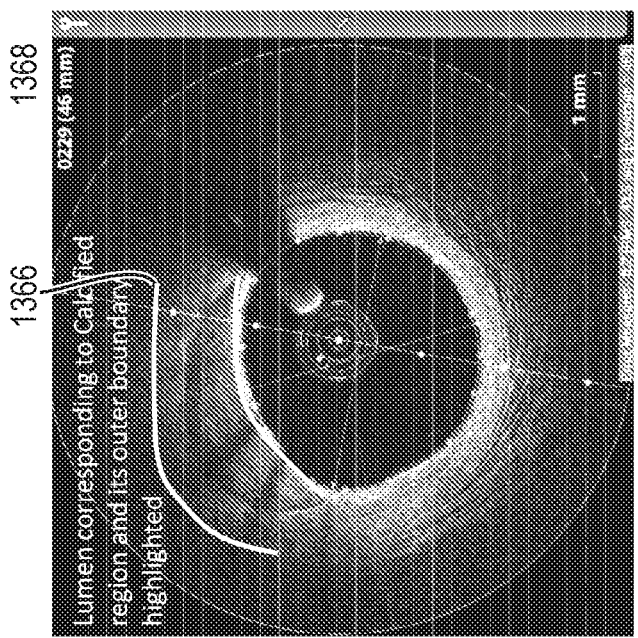
FIG. 13B is a cross-sectional OCT image with the inner and outer boundaries of the calcified region demarcated by bold lines.
Figure 13C:
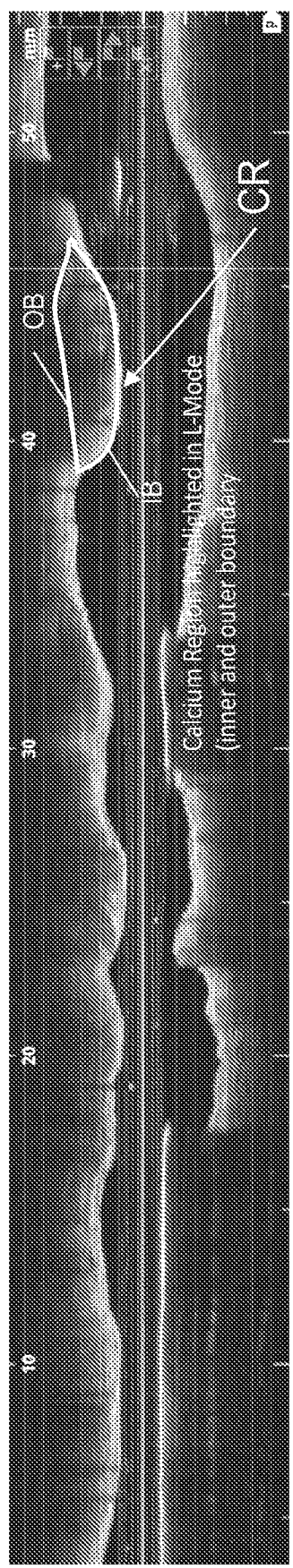
FIG. 13C is an L-Mode image showing the boundaries of the calcified region demarcated by bold lines.

FIG. 13A shows a further embodiment of a three dimensional rendering of a vessel lumen in which the calcified region has been volume rendered to provide a better estimation of plaque size. The CR frame 1 and CR frame N can also be depicted using an overlay or other graphic element. Various types of overlays and graphic elements can be used as shown in the figures and as described herein. As shown in FIG. 13B, the outer 1366 and inner 1368 boundaries of the calcified region are denoted by bold lines. FIG. 13C is an L-Mode image showing the inner 1366 and outer 1368 boundaries calcified region demarcated by bold lines. The boundary line segment 1368 is a lumen boundary. As shown in FIG. 13B, the lumen boundary 1368 which is adjacent the calcified region CR and adjacent a region of lumen that is bounded by line segment 1268. The outer boundary of the CR 1366 is also highlighted by line segment 1366. In FIG. 13C, an inner boundary IB and an outer boundary OB of the CR are also shown as computer generated line segments.

Figure 14B:
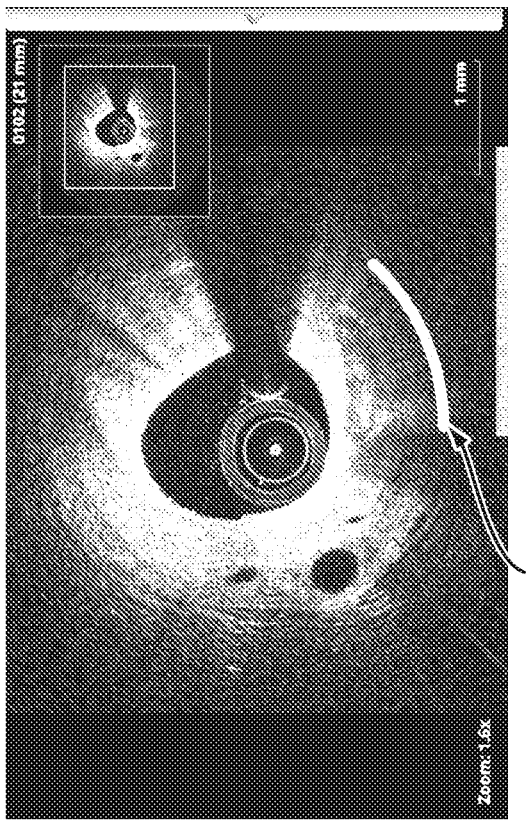
FIGS. 14A, 14B, and 14C show a graphic user interface that includes a left panel or screen (FIG. 14A), a right panel or screen (FIG. 14B), and a bottom panel or screen (FIG. 14C).
Figure 14A:
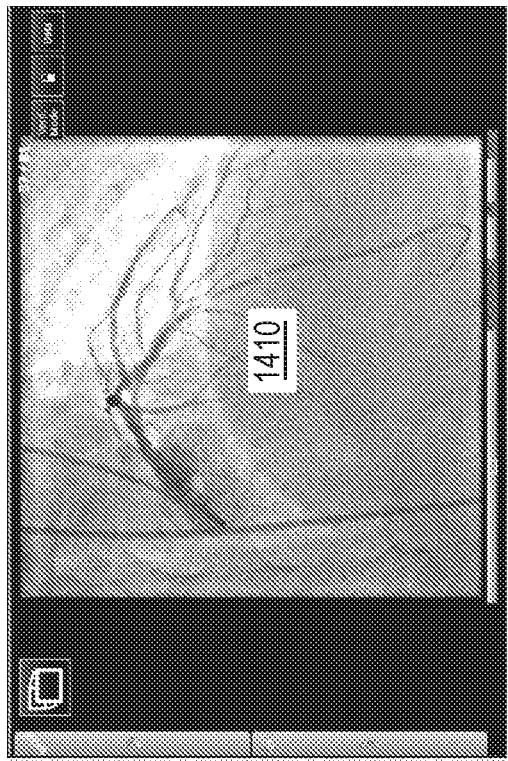

In FIG. 14A, intravascular data and angiography data are displayed with regard to a blood vessel. The top left panel or screen (FIG. 14A) shows an angiography image of a blood vessel. The top right panel (FIG. 14B) shows an optical coherence tomography image showing a cross-sectional view of the blood vessel along with an indicia 1420 relating to a calcified portion of the vessel. The bottom panel (FIG. 14C) shows an OCT image showing a longitudinal view of the vessel with the calcified region 1425 also shown. The longitudinal view also shows a dotted line 1430 corresponding to a reference vessel profile to guide expansion. The graphic representation of the guide to expansion is shown by indicia 1440. These indicia can be colors, lines, curves, symbols, and other suitable indicia.

Figure 14C:
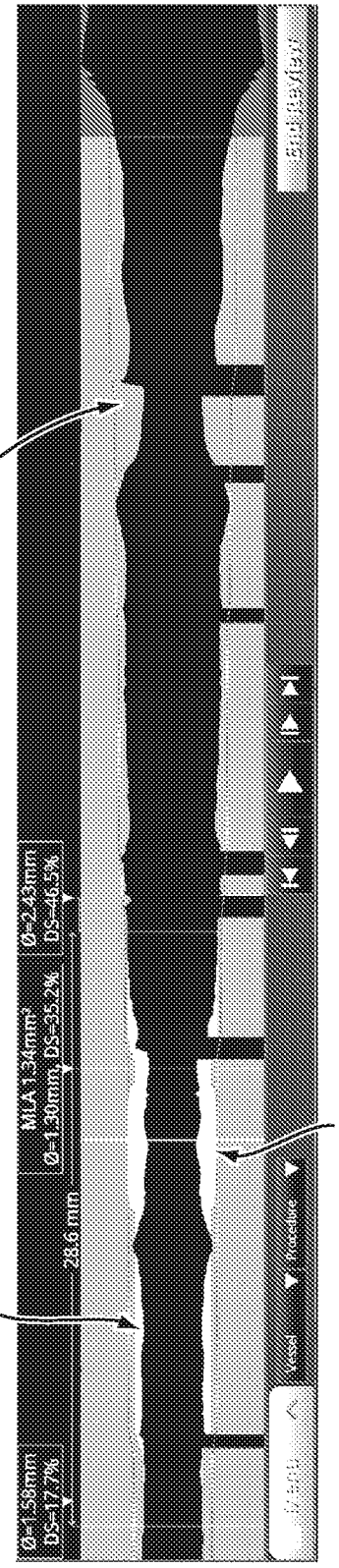

FIGS. 14A-C are suitable to help a user with additional information during lesion preparation by drawing attention to calcified vessel segments. The interface of FIGS. 14A-C also facilitates sizing of a stent or other device by providing a reference vessel profile 1430 to guide expansion 1440 of the device. In addition, FIG. 14's interface facilitates deployment of BVS or other stent or scaffold by displaying BVS position with angio coreg 1410 and generating scaffold apposition maps.

Figure 15A:
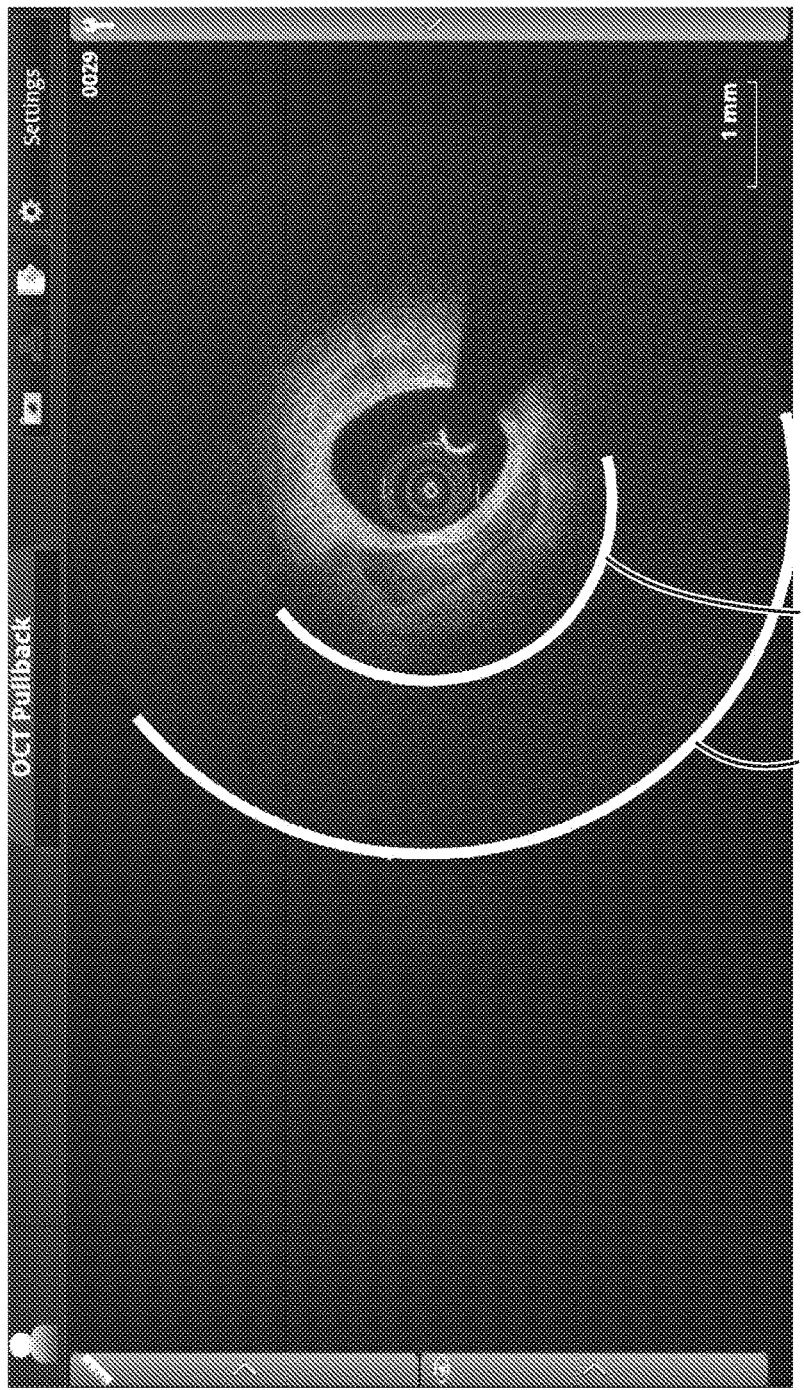
FIGS. 15A and 15B show a graphical user interface.

FIG. 15A shows an example screenshot with an exemplary plaque display graphical user interface (GUI). A calcified region has been detected and classified using an image processing-based approach described above. As shown, the calcium inclusion extends from approximately 6 o'clock to 10 o'clock in the OCT B-mode or cross-sectional image shown in the upper panel. The plaque display GUI superimposes a partial ring or arc 1510 on the OCT B-mode image corresponding to the circumferential extent of the calcium. The ring can be a circle or ellipse portion or other curve or other visualizable display element, symbol or icon. The radial position of the ring can be dynamically set to the imaging distance where the OCT signal intensity has decreased below a noise threshold such that there is no information content in the B-mode image.

In one embodiment, this use of indicia or other display elements to enhance visibility of a calcified region reduces screen clutter. The use of such indicia also enables placement of the plaque indicator relatively close to the plaque itself without obscuring OCT image features. Alternatively, the radial position can be set to a fixed value at the edge of the scan range 1512. These display techniques have the advantage that the position of the plaque can be clearly indicated without the need to draw a fully segmented or enclosed polygon around the lesion. Full segmentation can be technically challenging when the OCT signal does not extend fully to the back side of the plaque, which is common in intravascular applications. Plaque location and size information can also be displayed on the lumen profile section of the screen.

Figure 15B:
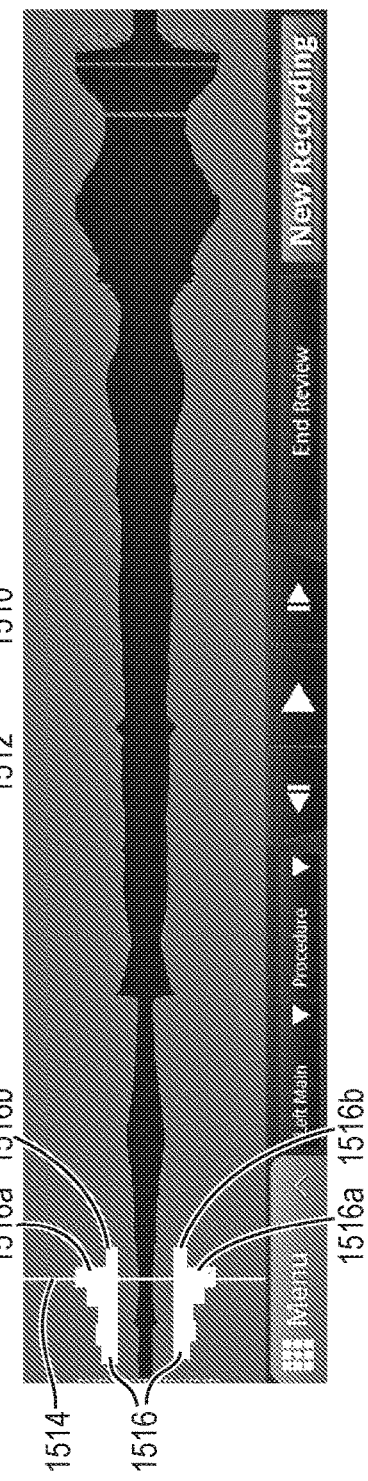

With reference to FIG. 15B, as shown in in longitudinal view, vertical bars 1516 can be placed on the lumen profile at positions corresponding to the cross-sectional frames where plaque was detected. As shown, in FIG. 15B, the sequence of bars are about the same for several frames and then step up and step down as shown. In FIG. 15B bar 1516a is the thickest and 1516b is the thinnest bar. The bars are shown as symmetric on either side of the lumen, but other representations such as only showing the bars above or below the lumen as well as others are possible.

In one embodiment, the height of the bars can be proportional to the circumferential extent of the plaque, such that a plaque which covers a larger circumference in cross-section is displayed as a vertically higher bar on the lumen profile display. In addition, a vertical line segment 1514 or bar or other indicia can be used to indicate the longitudinal position of the image shown in 15A relative to the cross-sectional view of FIG. 15B. This design allows the user to rapidly assess both the circumferential and longitudinal extent of the plaque by simple inspection of the lumen profile display.

Figure 16A:
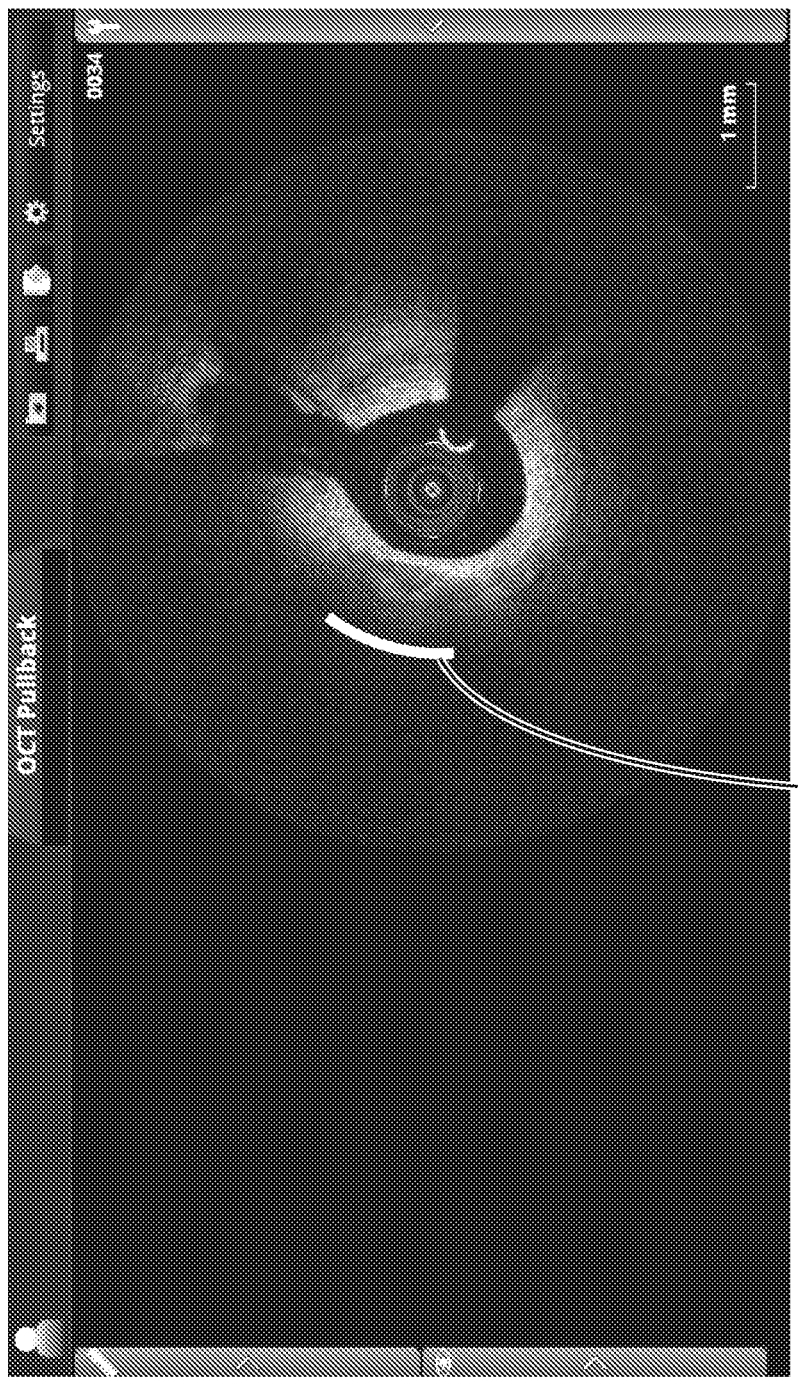
FIGS. 16A and 16B show a graphical user interface.
Figure 16B:
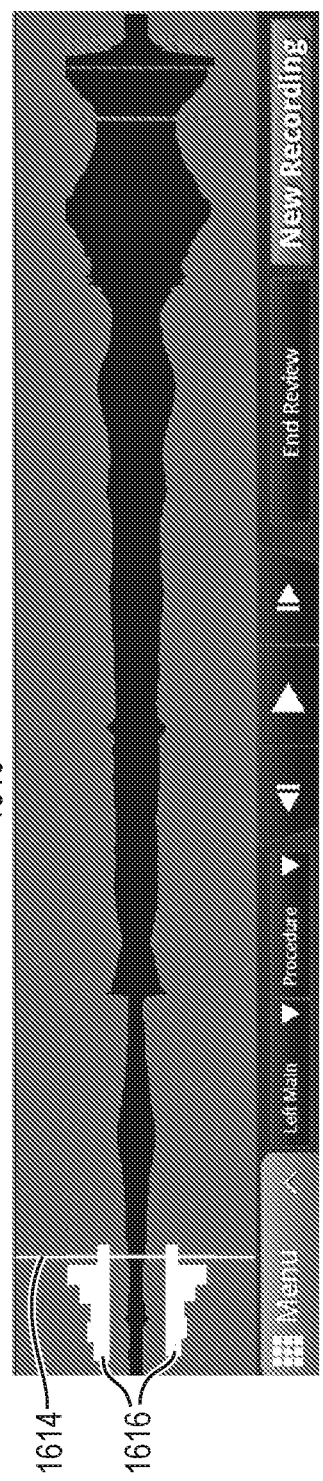

FIG. 16A shows an example of a different frame in the same pullback shown in FIG. 15A. In this frame, the calcium lesion extends only from approximately 9 o'clock to 10 o'clock. The vertical line 1614 is used to show the frame in FIG. 16B corresponding to the frame shown above in FIG. 16A. The partial ring 1610 on the B-mode image is therefore smaller than the ring 1610 on the previous frame, and the vertical bar 1616 is correspondingly smaller as well. Other methods and visible on screen elements can be generated using the GUI to enhance the on screen display of diagnostic information of interest with regard to the angiography data and the optical coherence tomography data.

The following description is intended to provide an overview of device hardware and other operating components suitable for performing the methods of the invention described herein. This description is not intended to limit the applicable environments or the scope of the invention. Similarly, the hardware and other operating components may be suitable as part of the apparatuses described above. The invention can be practiced with other system configurations, including personal computers, multiprocessor systems, microprocessor-based or programmable electronic devices, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "calculating" "interpolating" or "comparing" or "filtering" or "detecting" or "indicating" or "overlaying" or "sampling" or "operating" or "generating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention, in some embodiments, also relates to the apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the invention may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe, an FFR probe, an angiography system, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating OCT data, identifying calcified regions, performing image procession using various and other features and embodiments described herein.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, filtering, overlaying, generating indicia, line segments, and other graphic elements and overlays, routing and processing instructions, or various types of data such as OCT data, OCT polar image data, ROI measurements, cross-sectional images, polar images, IVUS data, shadows, calcified region frame or image data, boundary data, filter response data, pixels, intensity patterns, and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

The term "machine-readable medium" includes any medium that is capable of storing, encoding or carrying a set of instructions for execution by the machine and that cause the machine to perform any one or more of the methodologies of the present disclosure. While the machine-readable medium is shown in an example embodiment to be a single medium, the term "machine-readable medium" should be taken to include a single medium or multiple media (e.g., a database, one or more centralized or distributed databases and/or associated caches and servers) that store the one or more sets of instructions.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" or "substantially" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

The invention claimed is:

1. A system, comprising:
  a memory;
  one or more processors coupled to the memory, the one or more processors configured to:
    receive one or more images of a blood vessel;
    apply at least one edge detection filter to each of the one or more images to generate a filter response for each of the at least one edge detection filters;
    detect one or more maxima and a direction of each of the one or more maxima in each of the one or more filtered images;
    determine, based on the one or more maxima and the direction of each of the one or more maxima, a cluster in an image of the one or more filtered images;
    define, based on the cluster in the image, a region of interest;
    identifying the region of interest as a calcified region if the region of interest includes at least one vertical edge response maxima or identifying the region of interest as a non-calcified region of interest if the region of interest includes no vertical edge response maxima; and
    output a rendering of the blood vessel including an indication of the region of interest.

2. The system of claim 1, wherein the region of interest corresponds to a calcified region.

3. The system of claim 1, wherein when the detected one or more maxima and the direction of each of the one or more maxima includes at least one vertical edge response maxima.

4. The system of claim 1, wherein defining the region of interest further includes setting a bounding box on the cluster that corresponds to at least three directional filters.

5. The system of claim 4, wherein the at least three directional filters include one or more of an outer edge filter, an inner edge filter, a right edge filter, or a left edge filter.

6. The system of claim 1, wherein the output is a two-or three-dimensional model of the blood vessel using the one or more images and the detected one or more maxima and a direction of each of the one or more maxima.

7. A method, comprising:
receiving, by one or more processors, one or more images of a blood vessel;
applying, by the one or more processors, at least one edge detection filter to each of the one or more images to generate a filter response for each of the at least one edge detection filters;
detecting, by the one of more processors, one or more maxima and a direction of each of the one or more maxima in each of the one or more filtered images;
determining, by the one or more processors based on the one or more maxima and the direction of each of the one or more maxima, a cluster in an image of the one or more filtered images;
defining, by the one or more processor based on the cluster in the filtered image, a region of interest;
identifying the region of interest as a calcified region if the region of interest includes at least one vertical edge response maxima or identifying the region of interest as a non-calcified region of interest if the region of interest includes no vertical edge response maxima; and
outputting, by the one or more processors, a rendering of the blood vessel including an indication of the region of interest.

8. The method of claim 7, wherein the region of interest corresponds to a calcified region.

9. The method of claim 7, wherein when the detected one or more maxima and the direction of each of the one or more maxima includes at least one vertical edge response maxima.

10. The method of claim 7, wherein defining the region of interest further includes setting a bounding box, by the one or more processors, on the cluster that corresponds to at least three directional filters.

11. The method of claim 10, wherein the at least three directional filters includes at least one or more of an outer edge filter, an inner edge filter, a right edge filter, or a left edge filter.

12. The method of claim 7, further comprising:
determining, by the one or more processors based on the one or more maxima and the direction of each of the one or more maxima, an additional cluster in at least one additional filtered image of the one or more filtered images;
defining, by the one or more processors based on the additional cluster in the at least one additional filtered image, a second region of interest that corresponds to a calcified region; and
combining, by the one or more processors, the image and the at least one additional image.

13. The method of claim 7, wherein the output further includes a second indication of a group of the one or more images that do not include the region of interest.

14. The method of claim 7, wherein the output is a two-or three-dimensional model of the blood vessel using the one or more filtered images and the detected one or more maxima and a direction of each of the one or more maxima.

15. A non-transitory computer-readable medium storing instructions, which when executed by one or more processors, cause the one or more processors to:
receive one or more images of a blood vessel;
detect one or more maxima and a direction of each of the one or more maxima in each of the one or more images;
apply at least one edge detection filter to each of the one or more images to generate a filter response for each of the at least one edge detection filters;
detect one or more maxima and a direction of each of the one or more maxima in each of the one or more filtered images;
determine, based on the one or more maxima and the direction of each of the one or more maxima, a cluster in an image of the one or more filtered images;
define, based on the cluster in the image, a region of interest;
identify the region of interest as a calcified region if the region of interest includes at least one vertical edge response maxima or identifying the region of interest as a non-calcified region of interest if the region of interest includes no vertical edge response maxima; and
output a rendering of the blood vessel including an indication of the region of interest.

16. The non-transitory computer-readable medium of claim 15, wherein the region of interest corresponds to a calcified region.

17. The non-transitory computer-readable medium of claim 15, wherein when the detected one or more maxima and the direction of each of the one or more maxima includes at least one vertical edge response maxima.

18. The non-transitory computer-readable medium of claim 15, wherein defining the region of interest further includes setting a bounding box on the cluster that corresponds to at least three directional filters.

19. A system, comprising:
a memory;
one or more processors coupled to the memory, the one or more processors configured to:
receive one or more images of a blood vessel;
apply at least one edge detection filter to each of the one or more images to generate a filter response for each of the at least one edge detection filters;
detect one or more maxima and a direction of each of the one or more maxima in each of the one or more filtered images;
determine, based on the one or more maxima and the direction of each of the one or more maxima, a cluster in an image of the one or more filtered images;
define, based on the cluster in the image, a region of interest;
determine, based on the one or more maxima and the direction of each of the one or more maxima, an additional cluster in at least one additional filtered image of the one or more filtered images;
define, based on the additional cluster in the at least one additional image, a second region of interest that corresponds to a calcified region;
combine the image and the at least one additional image; and
output a rendering of the blood vessel including an indication of the region of interest.

20. The system of claim 19, wherein the region of interest corresponds to a calcified region.

21. The system of claim 19, wherein when the detected one or more maxima and the direction of each of the one or more maxima includes at least one vertical edge response maxima.

22. The system of claim 19, wherein defining the region of interest further includes setting a bounding box on the cluster that corresponds to at least three directional filters.

23. The system of claim 22, wherein the at least three directional filters include one or more of an outer edge filter, an inner edge filter, a right edge filter, or a left edge filter.

24. The system of claim 19, wherein the output further includes a second indication of a group of the one or more images that do not include the region of interest.

25. The system of claim 19, wherein the output is a two- or three-dimensional model of the blood vessel using the one or more images and the detected one or more maxima and a direction of each of the one or more maxima.

26. A system, comprising:
   a memory;
   one or more processors coupled to the memory, the one or more processors configured to:
      receive one or more images of a blood vessel;
      apply at least one edge detection filter to each of the one or more images to generate a filter response for each of the at least one edge detection filters;
      detect one or more maxima and a direction of each of the one or more maxima in each of the one or more filtered images;
      determine, based on the one or more maxima and the direction of each of the one or more maxima, a cluster in an image of the one or more filtered images;
      define, based on the cluster in the image, a region of interest; and
      output a rendering of the blood vessel including a first indication of the region of interest, and a second indication of a group of the one or more images that do not include the region of interest.

27. The system of claim 26, wherein the region of interest corresponds to a calcified region.

28. The system of claim 26, wherein when the detected one or more maxima and the direction of each of the one or more maxima includes at least one vertical edge response maxima.

29. The system of claim 26, wherein defining the region of interest further includes setting a bounding box on the cluster that corresponds to at least three directional filters.

30. The system of claim 29, wherein the at least three directional filters include one or more of an outer edge filter, an inner edge filter, a right edge filter, or a left edge filter.

31. The system of claim 26, wherein the one or more processors are further configured to:
   determine, based on the one or more maxima and the direction of each of the one or more maxima, an additional cluster in at least one additional filtered image of the one or more filtered images;
   define, based on the additional cluster in the at least one additional image, a second region of interest that corresponds to a calcified region; and
   combine the image and the at least one additional image.

32. The system of claim 26, wherein the output is a two- or three-dimensional model of the blood vessel using the one or more images and the detected one or more maxima and a direction of each of the one or more maxima.

* * * * *